(12) United States Patent
Dibble et al.

(10) Patent No.: US 9,403,915 B2
(45) Date of Patent: Aug. 2, 2016

(54) COMPOSITIONS AND METHODS USEFUL FOR IONIC LIQUID TREATMENT OF BIOMASS

(71) Applicants: Sandia Corporation, Livermore, CA (US); The Regents of the University of California, Oakland, CA (US)

(72) Inventors: Dean C. Dibble, San Mateo, CA (US); Aurelia Cheng, Cleveland Heights, OH (US); Anthe George, San Francisco, CA (US)

(73) Assignees: The Regents of the University of California, Oakland, CA (US); Sandia Corporation, Albuquerque, NM (US)

( * ) Notice: Subject to any disclaimer, the term of this patent is extended or adjusted under 35 U.S.C. 154(b) by 0 days.

(21) Appl. No.: 14/313,964

(22) Filed: Jun. 24, 2014

(65) Prior Publication Data
US 2014/0311481 A1    Oct. 23, 2014

Related U.S. Application Data

(62) Division of application No. 12/895,771, filed on Sep. 30, 2010, now Pat. No. 8,790,542.

(60) Provisional application No. 61/247,477, filed on Sep. 30, 2009.

(51) Int. Cl.
*C08B 1/00* (2006.01)
*C12P 19/02* (2006.01)

(52) U.S. Cl.
CPC ............... *C08B 1/003* (2013.01); *C12P 19/02* (2013.01); *C12P 2201/00* (2013.01); *Y02P 20/582* (2015.11)

(58) Field of Classification Search
CPC ........ C08B 1/003; C12P 19/02; C12P 2201/00
USPC .............. 127/34; 252/182.12; 435/41, 72, 99, 435/139, 140, 144, 145, 146, 157, 159, 160, 435/161, 162, 165, 174, 177, 179, 200, 209, 435/243, 252.1, 255.2, 255.5, 283.1, 294.1, 435/297.1; 554/174; 585/883
See application file for complete search history.

(56) References Cited

U.S. PATENT DOCUMENTS

| | | | |
|---|---|---|---|
| 4,038,481 A | 7/1977 | Antrim et al. | |
| 6,177,575 B1 | 1/2001 | Arduengo, III et al. | |
| 6,586,212 B1 | 7/2003 | Buchanan et al. | |
| 7,828,936 B2 * | 11/2010 | Luo et al. | 162/176 |
| 8,236,535 B2 * | 8/2012 | Medoff et al. | 435/162 |
| 8,598,378 B2 * | 12/2013 | Cooney et al. | 554/174 |
| 2004/0133058 A1 * | 7/2004 | Arlt et al. | 585/833 |
| 2007/0161095 A1 | 7/2007 | Gurin | |
| 2007/0259412 A1 | 11/2007 | Belanger et al. | |

(Continued)

OTHER PUBLICATIONS

S. S. Y. Tan, D. R. MacFarlane, Ionic Liquids in Biomass Processing Top. Curr. Chem. (2009) 290 311-339.

(Continued)

*Primary Examiner* — Peter F Godenschwager
*Assistant Examiner* — Andrew J Oyer
(74) *Attorney, Agent, or Firm* — Robin C. Chiang; Lawrence Berkeley National Laboratory

(57) ABSTRACT

The present invention provides for novel compositions and methods for recycling or recovering ionic liquid used in IL pretreated cellulose and/or lignocellulosic biomass (LBM).

10 Claims, 12 Drawing Sheets

(56) References Cited

U.S. PATENT DOCUMENTS

| | | |
|---|---|---|
| 2008/0190013 A1 | 8/2008 | Argyropoulos |
| 2009/0088564 A1* | 4/2009 | Luo et al. .................. 536/57 |
| 2009/0229599 A1 | 9/2009 | Zhang |

OTHER PUBLICATIONS

D. A. Fort, R. C. Remsing, R. P. Swatloski, P. Moyna, G. Moyna, R. D. Rogers, Can ionic liquids dissolve wood? Processing and analysis of lignocellulosic materials with 1-n-butyl-3-methylimidazolium chloride Green Chem. (2007) 9 63-69.

H. Zhao, C. L. Jones, G. A. Baker, S. Xia, O. Olubajo, V. N. Person, Regenerating cellulose from ionic liquids for an accelerated enzymatic hydrolysis J. Biotechnol. (2009) 139 47-54.

N. Sun, M. Rahman, Y. Qin, M. L. Maxim, H. Rodriguez, R. D. Rogers, Complete dissolution and partial delignification of wood in the ionic liquid 1-ethyl-3-methylimidazolium acetate Green Chem. (2009) 11 646-655.

I. Kilpeläinen, H. Xie, A. King, M. Granstrom, S. Heikkinen, D. S. Argyropoulos, Dissolution of Wood in Ionic Liquids J. Agric. Food Chem. (2007) 55 9142-9148.

M. Zavrel, D. Bross, M. Funke, J. Büchs, A. C. Spiess, High-throughput screening for ionic liquids dissolving (lingo-) cellulose Bioresour. Technol. (2009) 100 2580-2587.

Q. Li, Y.-C. He, M. Xian, G. Jun, X. Xu, J.-M. Yang, L.-Z. Li, Improving enzymatic hydrolysis of wheat straw using ionic liquid 1-ethyl-3-methyl imidazolium diethyl phosphate pretreatment Bioresour. Technol. (2009) 100 3570-3575.

Y. Wu, T. Sasaki, S. Irie, K. Sakurai, A novel biomass-ionic liquid platform for the utilization of native chitin Polymer (2008) 49 2321-2327.

H. Xie, S. Li, S. Zhang, Ionic liquids as novel solvents for the dissolution and blending of wool keratin fibers Green Chem. (2005) 7 606-608.

N. Kamiya, Y. Matsushita, M. Hanaki, K. Nakashima, M. Narita, M. Goto, H. Takahashi, Enzymatic in situ saccharification of cellulose in aqueous-ionic liquid media Biotechnol. Lett. (2008) 30 1037-1040.

C. Li, Q. Wang, Z. K. Zhao, Acid in ionic liquid: An efficient system for hydrolysis of lignocellulose Green Chem. (2008) 10 177-182.

M. Mazza, D.-A. Catana, C. Vaca-Garcia, C. Cecutti, Influence of water on the dissolution of cellulose in selected ionic liquids Cellulose (2009) 16 207-215.

H. G. Joglekar, I. Rahman, B. D. Kulkarni, The Path Ahead for Ionic Liquids Chem. Eng. Technol. (2007) 30 No. 7 819-828.

K. E. Gutowski, G. A. Broker, H. D. Willauer, J. G. Huddleston, R. P. Swatloski, J. D. Holbrey, R.D. Rogers, Controlling the Aqueous Miscibility of Ionic Liquids: Aqueous Biphasic Systems of Water-Miscible Ionic Liquids and Water-Structuring Salts for Recycle, Metathesis, and Separations J. Am. Chem. Soc. (2003) 125 6632-6633.

S. Li, C. He, H. Liu, K. Li, F. Liu, Ionic liquid-based aqueous two-phase system, a sample pretreatment procedure prior to high-performance liquid chromatography of opium alkaloids J. Chromatogr. B (2005) 826 58-62.

X. Honglu, S. Tiejun, Wood liquefaction by ionic liquids Holzforschung (2006) 60 509-512.

O. Aaltonen, O. Jauhiainen, The preparation of lignocellulosic aerogels from ionic liquid solutions Carbohydr. Polym. (2009) 75 125-129.

J. Kadokawa, M. Murakami, A. Kaneko, A facile preparation of gel materials from a solution of cellulose in ionic liquid Carbohydr. Res. (2008) 343 769-772.

A. Pinkert, K. N. Marsh, S. Pang, M. P. Staiger, Ionic Liquids and Their Interaction with Cellulose Chem. Rev. (2009) 109 6712-6728.

L. Zhang, J. Han, D. Deng, J. Ji, Selection of ionic liquids as entrainers for separation of water and 2-propanol Fluid Phase Equilib. (2007) 255 179-185.

F. Montañés, A. Olano, E. lbáez, T. Fornari, Modeling Solubilities of Sugars in Alcohols Based on Original Experimental Data AIChE J. (2007) 53 No. 9 2411-2418.

M. Deng, Q. Zhou, A. Du, J. van Kasteren, Y. Wang, Preparation of nanoporous cellulose foams from cellulose-ionic liquid solutions Mater. Lett. (2009) 63 1851-1854.

K. Thammasouk, D. Tandjo, M. H. Penner, Influence of Extractives on the Analysis of Herbaceous Biomass J. Agric. Food Chem. (1997) 45 437-443.

\* cited by examiner

COMPOSITIONS AND METHODS USEFUL FOR IONIC LIQUID TREATMENT OF BIOMASS

CROSS-REFERENCE TO RELATED APPLICATIONS

This application claims priority as a divisional application to U.S. patent application Ser. No. 12/895,771, filed Sep. 30, 2010, which claims priority to U.S. Provisional Patent Application Ser. No. 61/247,477, filed Sep. 30, 2009, which is hereby incorporated by reference.

STATEMENT OF GOVERNMENTAL SUPPORT

The invention was made with government support under Contract Nos. DE-AC02-05CH11231 and DE-AC04-94AL85000 awarded by the U.S. Department of Energy. The government has certain rights in the invention.

FIELD OF THE INVENTION

The present invention is in the field of pretreatment of biomass using ionic liquid.

BACKGROUND OF THE INVENTION

Biomass pretreatment for conversion to sugars remains one of the most challenging obstacles to the design of an economically viable bi-refinery for biofuel production. Several pretreatments and biomass fractionation technologies exist or are under consideration. A promising new candidate technology for biomass fractionation is ionic liquid (IL) pretreatment. In the IL pretreatment process, biomass is dissolved in an IL and carbohydrates, such as hemicellulose and cellulose, are precipitated on the addition of an anti-solvent, such as water. The regenerated cellulose possesses an amorphous structure that is especially amendable to enzymatic saccharification and may contain little or no inhibitory components for subsequent processing to a biofuel.

The most common approach to recover the ionic liquid is to simply distill off solvents (including water) that dilute ionic liquids or are formed as byproducts of reactions carried out in ionic liquids. While this is a simple and effective approach, it is also very energy intensive, especially when low concentrations of ionic liquid are encountered, or when the processing scale becomes large. Currently, there is nothing in the literature indicating any IL recovery approach involving solvents other than removal by distillation/evaporation except in the few cases where reactants or products are miscible in a second, immiscible liquid added for the purpose of reactant, product, or IL recovery.

The use of hydrocarbon solvents in ionic-liquid processing of cellulose is generally not emphasized in the literature because they are not as 'green' and approach as could be desired. All literature references I am familiar with describe ionic liquid recovery in terms of distilling off the precipitating solvent. No mention anywhere is made of the difficulty of recycling ionic liquid from the more dilute solutions resulting from 'wash' steps or other procedures designed to recover the relatively expensive ionic liquid from the inexpensive product stream.

Currently, different precipitating agents are used, but all involve the formation of a gel phase at low precipitating solvent concentrations and high cellulose or biomass solute concentrations. This is usually compensated for by increasing the amount of precipitating solvent used, but there are process costs associated with this additional solvent, and these can be minimized by working in the narrow phase region that we have discovered. We believe that the solvent mixture that we have found results in the minimum amount of precipitating solvent and a maximum quantity of dissolved cellulose or biomass to be used in a process, and is clearly superior to use of a single solvent or mixture outside of the specific composition range described below.

There is no generally known method of extracting lignin and sugars from ionic liquids used in ionic liquid biomass pretreatment. For some other processes, there have been ionic-liquid immiscible solvents found where the partitioning coefficients of the desired solutes are appropriate for liquid-liquid extraction. In some other chemical processes a product may be removed thermally (as a vapor) or can undergo a chemical reaction to form a solid product. However, none of these approaches is applicable to ILs that are useful solvents for biomass.

The present invention overcomes these issues.

SUMMARY OF THE INVENTION

The present invention provides for novel compositions and methods for recycling or recovering ionic liquid used in IL pretreated cellulose and/or lignocellulosic biomass (LBM).

The present invention provides for a composition formed from contacting (a) a first solution comprising a water-miscible ionic liquid (IL), a polar-aprotic solvent, optionally a weak hydrogen bonding solvent, and optionally a biomass, lignin, or cellulose; and (b) a polar-protic solvent; wherein the composition comprises (i) first liquid phase and (ii) a solid or second liquid phase.

The present invention provides for a method comprising one or more of the steps described in Example 1 herein.

The present invention also provides for a composition comprising an IL, a ketone, an alcohol, and optionally a solid biomass or cellulose, wherein the ratio of the IL:ketone:alcohol is as defined with the area labeled "Porous Solid+Liquid" in FIG. 3. In some embodiments, the alcohol can be partially, or optionally wholly if not water) replaced by any other polar-protic solvent, including but not limited to partial replacement with water. In some embodiments, 95% v/v ethanol can be used, and so long as the sum of moles of alcohol and water falls within the range of "Porous Solid+Liquid" defined in FIG. 3 then the solution is effective. Practically, light alcohols will likely be used for biomass pretreatment because of their low cost, but for other applications other proton-donor solvents (such as weak organic acids) can also be used in the process.

The present invention also provides for a method comprising one or more of the steps described in Example 2 herein. The method comprises: contacting or mixing (i) a first solution comprising a ionic liquid (IL) and a biomass or a cellulose, and (ii) a second solution comprising a ketone and an alcohol solution to form a third solution, wherein the biomass or cellulose precipitates or becomes solid and the third solution does not form a gel or have a viscous intermediate phase. The second solution is a precipitating solution. The third solution is a precipitating mixture. In some embodiments, the method further comprises: separating the solid biomass or cellulose from the liquid portion of the third solution.

The present invention further provides for a system comprising a ketone, an alcohol, an ionic liquid (IL), and water, which makes use of the phase splitting capability of the system. The system will phase split with or without solutes. Solutes will modify the behavior, and may be used advantageously for solute fractionation, but even a pure IL/ketone/alcohol/water system will phase split in the right proportions.

The present invention further provides for a method comprising one or more of the steps described in Example 3 herein.

The present invention further provides for a method comprising one or more of the steps described in Example 4 herein.

The present invention provides for a composition comprising a ketone (such as acetone), a suitable alcohol (such as ethanol), precipitated cellulose and/or lignocellulosic biomass (LBM), and an ionic liquid (IL), wherein there is no formation of an intermediate gel phase.

The present invention also provides for a method of recycling ionic liquid (IL) in a pretreatment process, comprising: (a) providing a first solution comprising cellulose and/or LBM, an IL, a ketone and an alcohol in a molar ratio defined herein such that the cellulose and/or LBM are solid or precipitated, (b) washing the second solution with an alcohol wash to produce a solid portion and a liquid portion, wherein the solid portion comprises the precipitated cellulose and/or LBM, (c) separating the solid portion and the liquid portion, (d) adding a Cascade Wash B, comprising 2-propanol, to the liquid portion, (e) distilling the liquid porton to remove at least a portion of the ketone and the 2-propanol, (f) adding acetone to the remaining liquid from step (e) to form a first extract, (g) adding a mixture of a ketone and 2-propanol to form a second extract, (h) extracting the IL in the first and second extracts, and (i) extracting lignin from the remainder of the remaining after the removal of the first and second extracts. Particular embodiments of this method are described in Example 4 and FIG. 14.

The ketone can be extracted from the liquid portion of step (c) through distilling the liquid portion. The alcohol can be extracted from the solid portion of step (c) through drying the solid or precipitates and collecting the evaporated alcohol.

The suitable composition range for solvents that will precipitate cellulose and/or LBM can be expressed as a molar ratio X:Y:Z::ketone (such as acetone):alcohol (such as ethanol):IL (such as [C2mim][OAc]), with about X>3, 0.8<Y<1.2, and Z=1 for normalization. In some embodiments, the molar ratio is about 3.3≤X≤8, Y≈1, and Z=1 as before. In some embodiments, the molar ratio is about 4≤X≤6, Y=1, and Z=1. In a particular embodiment, the solution or composition capable of precipitating cellulose and/or LBM (such as from an about 15 weight-% cellulose solution in [C2mim][OAc] using a mixture of acetone and methanol) comprises a molar ratio about X=3.3, Y=1, and Z=1. The precipitate produced is solid or powdery and can be separated by filtration.

The invention also provides for any of the novel solutions and/or mixtures described herein.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "IL" includes a single IL compound as well as a plurality of IL compounds, either the same (e.g., the same molecule) or different.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The present invention provides for a composition formed from contacting (a) a first solution comprising a water-miscible ionic liquid (IL), a polar-aprotic solvent, optionally a weak hydrogen bonding solvent, and optionally a biomass, lignin, or cellulose; and (b) a polar-protic solvent; wherein the composition comprises (i) first liquid phase and (ii) a solid or second liquid phase.

The present invention provides for a method comprising one or more of the steps described in Example 1 herein.

Figure 3:
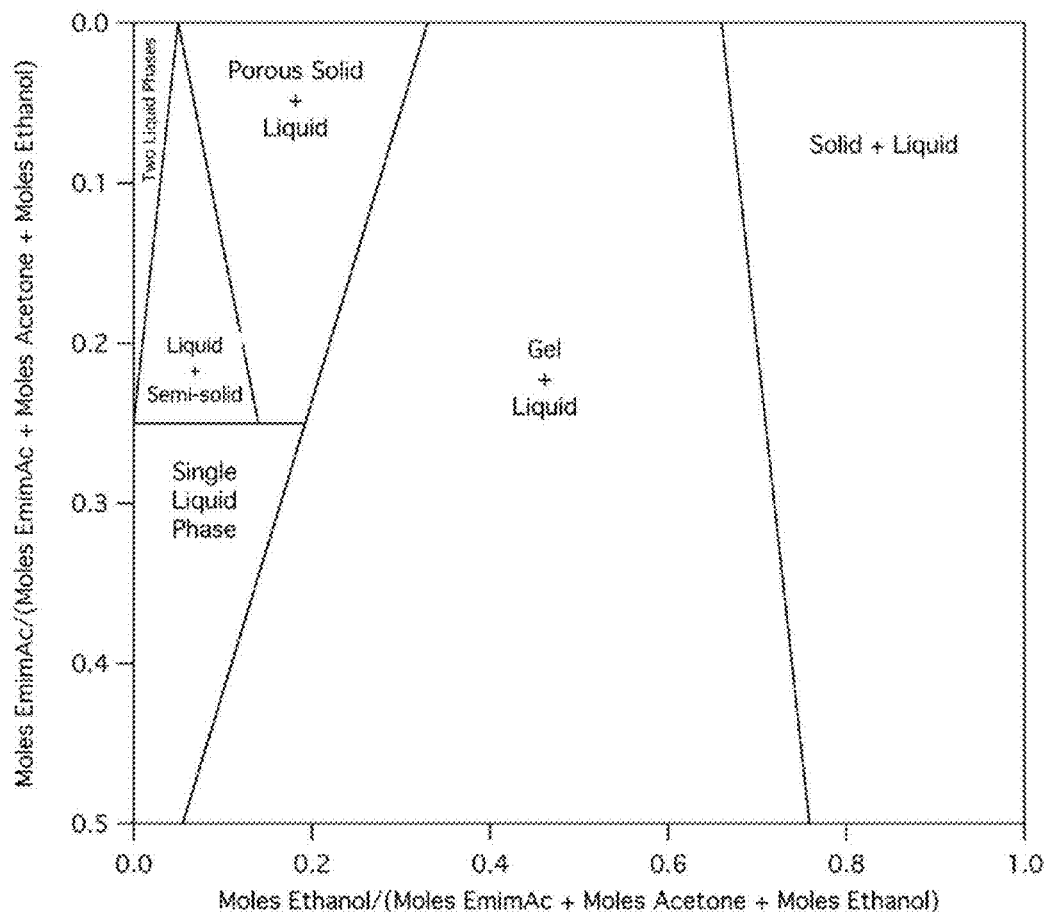
FIG. 3 shows the B+W plots of phase diagrams for the ethanol/acetone/EMIM Acetate/cellulose system. The area one should operate is designated as the "porous solid+liquid" region wherein a biomass precipitating solvent that does not form a gel phase.

The present invention also provides for a composition comprising an IL, a ketone, an alcohol, and optionally a solid biomass or cellulose, wherein the ratio of the IL:ketone:alcohol is as defined with the area labeled "Porous Solid+Liquid" in FIG. 3.

The present invention also provides for a method comprising one or more of the steps described in Example 2 herein. The method comprises: contacting or mixing (i) a first solution comprising a ionic liquid (IL) and a biomass or a cellulose, and (ii) a second solution comprising a ketone and an alcohol solution to form a third solution, wherein the biomass or cellulose precipitates or becomes solid and the third solution does not form a gel or have a viscous intermediate phase. The second solution is a precipitating solution. The third solution is a precipitating mixture. In some embodiments, the method further comprises: separating the solid biomass or cellulose from the liquid portion of the third solution.

The present invention further provides for a system comprising a ketone, an alcohol, an ionic liquid (IL), and water, which makes use of the phase splitting capability of the system in the presence or absence of substantial quantities of solutes.

The present invention further provides for a method comprising one or more of the steps described in Example 3 herein.

In some embodiments of the invention, the ketone is acetone, dimethyl ketone, methyl-ethyl ketone, diethyl ketone, or the like, or a mixture thereof. In some embodiments, the alcohol is methanol, ethanol, propanol, butanol, or the like, or a mixture thereof.

In some embodiments, the IL is any suitable IL, or a mixture thereof, described herein. Suitable IL are taught in ChemFiles (2006) 6(9) (which are commercially available from Sigma-Aldrich; Milwaukee, Wis.). Such suitable IL include, 1-alkyl-3-alkylimidazolium alkanate, 1-alkyl-3-alkylimidazolium alkylsulfate, 1-alkyl-3-alkylimidazolium methylsulfonate, 1-alkyl-3-alkylimidazolium hydrogensulfate, 1-alkyl-3-alkylimidazolium thiocyanate, and 1-alkyl-3-alkylimidazolium halide, wherein an "alkyl" is an alkyl group comprising from 1 to 10 carbon atoms, and an "alkanate" is an alkanate comprising from 1 to 10 carbon atoms. In some embodiments, the "alkyl" is an alkyl group comprising from 1 to 4 carbon atoms. In some embodiments, the "alkyl" is a methyl group, ethyl group or butyl group. In some embodiments, the "alkanate" is an alkanate comprising from 1 to 4 carbon atoms. In some embodiments, the "alkanate" is an acetate. In some embodiments, the halide is chloride.

Suitable IL include, but are limited to, 1-ethyl-3-methylimidazolium acetate (EMIN Acetate), 1-ethyl-3-methylimidazolium chloride (EMIN Cl), 1-ethyl-3-methylimidazolium hydrogensulfate (EMIM HOSO$_3$), 1-ethyl-3-methylimidazolium methylsulfate (EMIM MeOSO$_3$), 1-ethyl-3-methylimidazolium ethylsulfate (EMIM EtOSO$_3$), 1-ethyl-3-methylimidazolium methanesulfonate (EMIM MeSO$_3$), 1-ethyl-3-methylimidazolium tetrachloroaluminate (EMIM AlCl$_4$), 1-ethyl-3-methylimidazolium thiocyanate (EMIM SCN), 1-butyl-3-methylimidazolium acetate (BMIM Acetate), 1-butyl-3-methylimidazolium chloride (BMIM Cl), 1-butyl-3-methylimidazolium hydrogensulfate (BMIM HOSO$_3$), 1-butyl-3-methylimidazolium methanesulfonate (BMIM MeSO$_3$), 1-butyl-3-methylimidazolium methylsulfate (BMIM MeOSO$_3$), 1-butyl-3-methylimidazolium tetrachloroaluminate (BMIM AlCl$_4$), 1-butyl-3-methylimidazolium thiocyanate (BMIM SCN), 1-ethyl-2,3-dimethylimidazolium ethylsulfate (EDIM EtOSO$_3$), Tris(2-hydroxyethyl)methylammonium methylsulfate (MTEOA MeOSO$_3$), 1-methylimidazolium chloride (MIM Cl), 1-methylimidazolium hydrogensulfate (MIM HOSO$_3$), 1,2,4-trimethylpyrazolium methylsulfate, tributylmethylammonium methylsulfate, choline acetate, choline salicylate, and the like. Further ILs are taught in U.S. Pat. No. 6,177,575, herein incorporated by reference. Suitable ILs also include, but is not limited to, carboxylate anions of all types, such as lactate, maleate, and other organic acids with or without additional hydroxyl groups at different positions within the anion, and di-alkylphosphates, such as dimethylphosphate, diethylphosphates, or mono- or di-alkyl phosphate anions with or without the same groups, i.e. methyl-ethyl-phosphate (phosphonate) anions.

In the methods described herein any separating of a solid and a liquid can comprise filtrating, decantation, centrifugating, or the like, or a combination thereof.

In some embodiments of the invention, the biomass is a cellulose biomass, hemicellulose biomass, ligno-cellulose biomass, or a mixture thereof.

The invention also provides for any of the novel solutions and/or mixtures described herein.

In some embodiments of the invention, the biomass is a cellulose biomass, hemicellulose biomass, ligno-cellulose biomass, or a mixture thereof. The biomass can be an untreated or treated biomass.

Applications

The present invention can be used any chemical, pharmaceutical, biofuel, or other industrial application that either is or is considering using ILs as part of their process, such as research, commercial manufacturing, and perhaps even large scale processing of commodity materials and fuel. The process is of significant interest in biomass processing or biofuels and other biomaterials, paper recycling and pulp processing for paper manufacturing.

This technology can be used for the fractionation and purification of ILs and solutes dissolved in ILs. The most obvious application is in the separation and recovery of IL, lignin, and sugars dissolved in ILs as part of an IL biomass pretreatment process. There are many industrial and specialty chemical processes that are taking advantage of ILs and where product separation and isolation would benefit from the idea described in this disclosure.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

EXAMPLE 1

Solvent Displacement Reactions with Hydrogen Bond Donors Solvents as a Means of IL Recovery or Separation from Miscible Solvents The basic concept is that a mixture of at least two components, a hydrophilic ionic liquid, and a polar-aprotic solvent (other species may be present), can phase separate into at least two liquid phases or a liquid and solid phase on addition of a hydrogen-bonding solvent. Additional materials present in solution (added intentionally or desirable or undesirable products) can modify this phase separation behavior in a predictable and useful way. One application of this invention is the concentration and recovery of ionic liquid from a mixture of ionic liquid, alcohol, and a ketone used for precipitating and washing cellulose or biomass from a biomass pretreatment process and for the recovery of lignin dissolved in an ionic liquid. Because other species present in solution partition differently into the two different phases produced by the addition of a hydrogen-bonding solvent, this reaction can be used for purification or fractionation of mixtures dissolved in an ionic liquid or ionic liquid mixture. Additionally, the reaction that produces the second phase is sensitive to the strength of the alcohol, ketone, or other co-solvent interaction with the ionic liquid cation or anion and can therefore be used to concentrate or separate mutually miscible ionic liquids from each other. This approach could be applied to the fractionation, concentration, or separation of materials with different solubility in different but miscible ionic liquids.

The method provides a new pathway for separating miscible compounds, including miscible ILs) with low vapor pressure from an IL. The method comprises concentrating and separating an IL from a larger quantity of miscible solvent without resorting to distilling off the solvent. This method can also be used to fractionate mixtures of ILs without using column chromatography, or repeat liquid-liquid extraction steps, or forming an intermediate product that could be used to recover the IL chemically.

It was not obvious what the solvent coordination behavior for ionic liquid cations or anions would look like, or that the replacement of a solvation shell of one chemical species with another in an ionic liquid would comprise advantageous liquid-liquid phase behavior. For the system described herein (IL, such as EMIM Acetate, Acetone, Water, Ethanol), the extremely large impact of very small quantities of water masked the real behavior because of the natural tendency of all these non-aqueous solvents to absorb water from the ambient atmosphere.

Figure 1:
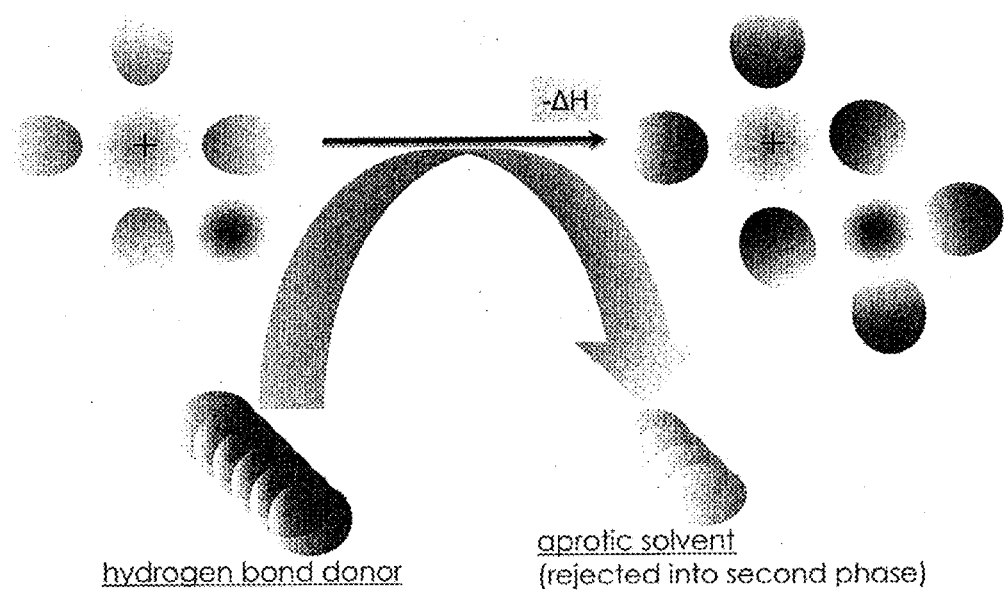
FIG. 1 shows replacement and phase separation of a polar aprotic IL solvent with a second moiety with stronger hydrogen bond donor characteristics.

FIG. 1 shows replacement and phase separation of a polar aprotic IL solvent with a second moiety with stronger hydrogen bond donor characteristics.

Figure 2:
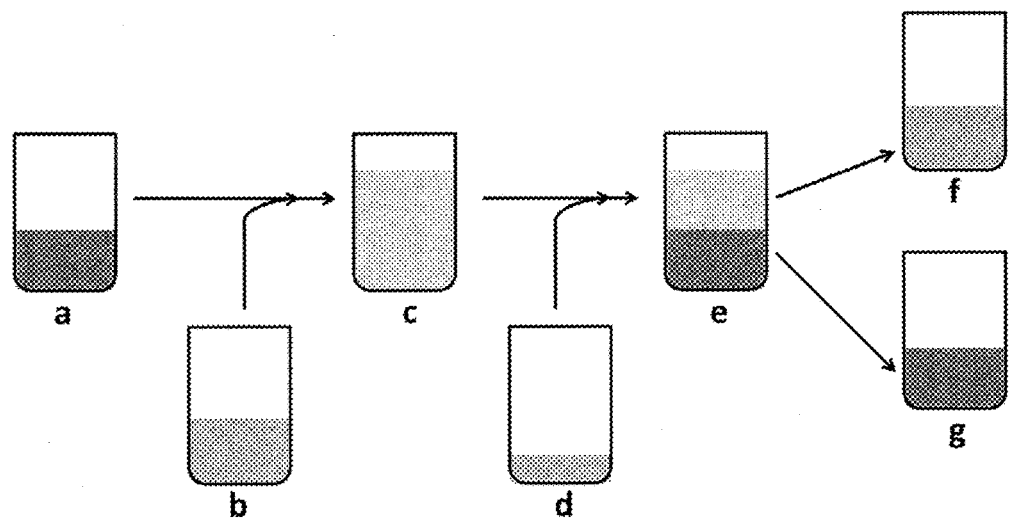
FIG. 2 shows a scheme for solvent displacement/phase switching. "a" is a water-miscible IL that optionally contains a small quantity of hydrogen-bond forming substances. "b" is a polar aprotic solvent that optionally also contains a small quantity of hydrogen-bond forming substances. "c" is the single phase solution formed from the combining of "a" and "b". "d" is a polar-protic solvent (such as water, an amine, a hydroxyl-containing substance, or a mixture thereof). "e" is a two-phase liquid mixture. "f" and "g" the liquid phases separated from "e" by decantation or any other means.

FIG. 2 shows a scheme for solvent displacement/phase switching. "a" is a water-miscible IL. Experiments are performed with EMIM Acetate but the method can be applied to any IL. The IL maybe at an intermediate or end of a synthesis, fractionation, absorption, other any other chemical process. IL may comprise of a mixture of more than one miscible ILs. Il may contain one or more solutes, reaction products, co-solvents, or other dissolved species.

"b" is a polar aprotic solvent that optionally contains a small quantity of hydrogen-bond forming substances. Experiments are performed using acetone and acetone/ketone mixtures. Methyl-ethyl ketone, other alcohols and other ketones, carbonyl-group containing substances, amines, and other materials can also be used. The addition of a weak hydrogen-bond donating solvent to "b" can be desirable or necessary to form a single phase solution at "c". Such example include alcohols, weak acids, and other amine or hydroxyl-containing species that are poorly ionized at the conditions present in the solution. The polar aprotic solvent chosen, and the species and quantity of hydrogen-bonding solutions can be routinely determined through the use of ternary and quaternary phase diagrams. The polar aprotic solvent forms a coordination complex with the IL cation and the polar aprotic solvent should be chosen with a size and dipole properties that permit this to happen. The weak hydrogen-bond donor acts as a co-solvent for the polar-aprotic solvent, the IL, and any hydrogen-bond donating solutes or water present in the IL. Alcohol can be the weak hydrogen-bond donor, wherein a single phase solution can be maintained in the presence of increasing levels of strong hydrogen-bond donors (such as water) by increasing the concentration of alcohol.

"c" is the single phase solution formed from the combining of "a" and "b". Depending on the process, precipitation of a solute originally present in "a" may form, and can be separated by a solid-liquid separation process (such as filtration, centrifugation, and the like). For cellulose or biomass dissolved in EMIM Acetate, the precipitation of cellulose-rich material occurs at this stage of processing and can be removed by filtration, decantation, centrifugation, or the like.

"d" is a polar-protic solvent (such as water, an amine, a hydroxyl-containing substance, or a mixture thereof). Water may be the most desirable and optimum material for this stage. The molar quantity necessary depends on the cation, anion, and whether it is water or other protic solvent used. For water in EMIM Acetate it is about 6 moles water/mole IL. For different ILs the ratio can be determined by routine methods taught in the present application. Smaller or larger quantities can be used to fractionate solutes, concentrate, or separate miscible ILs, etc. In some embodiments, for maximum separation, sufficient water is necessary to form a complete hydration shell around the cation and anion; the precise amount varies with different cations and anions.

"e" is a two-phase liquid mixture. Additional solutes may precipitate in either phase at this process stage and be separated by solid-liquid separation. Liquid phases can be separated by decantation or other means. Solutes dissolved in "c" partition according to their solubility in the two liquid phases. For pure simple systems, the quantity of liquid in each phase is very sensitive to the quantity of polar protic solvent "d" added when near its phase separation concentration. For systems with considerable dissolved solutes, the sensitivity to quantity of protic solvent "d" added to form a second liquid phase maybe much less than in pure simple system. This can be used to selectively precipitate, or fractionate, liquid phases with variable concentrations or species of solute. This process can be used concentrate lignin dissolved in an IL, and also to isolate breakdown products of the IL. "f" and "g" the liquid phases separated from "e" by decantation or any other means.

EXAMPLE 2

Recovery of Dry, Amorphous, High Surface Area Biomass from a IL Solution without Formation of Gel-Phase Intermediate For ionic liquid solutions containing dissolved cellulose or biomass, the addition of a mixture of a ketone and an alcohol in the right proportion will cause the precipitation of a cellulose or cellulose-rich biomass material without forming an intermediate gel or otherwise highly viscous intermediate phase and will form a precipitate that has a high surface area, is easy to filter, and has low tendency to form aggregates. The quantity of ketone used is determined by the number of solvent molecules in the inner solvation shell of the ionic liquid cation. For the ionic liquid 1-ethyl-3-methyl imidazolium acetate, and probably all N,N'-alkyl imidazolium based ionic liquids, greater than 3 moles/mole of ketone per IL cation is required. An optimum quantity is from 3 to 4 moles ketone/mole ionic liquid cation. An alcohol added to a concentration of 0.9-1.0 moles/mole IL cation must also be included in the mixture. For 0.9-1.0 mole of alcohol, some fraction could be water so long as the sum of the moles of alcohol and the moles of water is about 0.9-1.0. For pure cellulose dissolved in ILs the desirable quantity of alcohol is close to 1.0 mole/mole. For biomass with significant quantities of lignin dissolved in an IL the quantity may be slightly less. The ketone/alcohol mixture can be created prior to the addition of IL/cellulose solution, or the ketone may be added to the IL solution, followed by the alcohol. The alcohol should not be added first, or at higher concentrations than ~1 mole/mole IL cation or a gel phase will result. The strength of the gel phase is proportional to the quantity and degree of polymerization of the dissolved cellulose and lignin in the IL. Suitable ketones are acetone, methyl-ethyl ketone, pentanone, cyclopentanone, and other substances that do not include an adjacent nitrogen atom near the keto-functional group or that contain a —OH (hydroxyl) group on the molecule. Suitable alcohols are methanol, ethanol, propanol, butanol, and the like. There may exist a molecule with both ketone and alcohol functionalities that can be partially or completely substituted for some or all of the alcohol and some of the ketone.

Moderately increasing the alcohol content leads to the formation of a gel phase that complicates liquid-solid separation processes. Greatly increasing alcohol content or adding another hydrogen bond donor solvent such as water such that the sum of moles of hydrogen bond donor solvents greatly exceeds 1.0 mole/mole ionic liquid may eventually eliminate the gel phase, but will not prevent the gel phase from forming during the addition process. It is usually desirable, especially for processing biomass, to minimize the amount of precipitating solvent used. Adding less that the specified amount of alcohol described here leads to either a sticky semi-solid precipitate that is difficult to filter, the formation of two liquid phases, or no precipitation of cellulose and lignin dissolved in the ionic liquid. Adding less than ~3 moles ketone/mole IL cation results in either no precipitation of cellulose or biomass or the formation of a gel phase depending on the quantity of alcohol added.

This method allows IL biomass processing at higher biomass loadings than were previously possible while still producing a highly porous, high surface area product. At high biomass or cellulose loadings, the gel phase that occurs during addition of a hydrogen bond-donating solvent (such as an alcohol or water) can be much more "solid" or require much higher levels of energy for mixing than either the initial ionic liquid/biomass solution or the two-phase mixture that results after precipitation. The stiffness of gels at biomass loadings higher than about 5% make the mixing of precipitating solvent extremely difficult and typically generates a stringy, low porosity product material when dried. Using water as an anti-solvent results in a product that cannot be dried without an additional solvent exchange step or a hard, plastic-like material results with low accessible surface area and poor enzymatic digestibility. Within a specific range of composition, an ethanol/acetone mixture results in a porous, easy to filter, low density solid that dries to a high surface area floc or powder. Even with very high cellulose loadings (such as 15% w/w cellulose in the IL ethylmethyl imidazolium acetate) addition of this solvent mixture produces a precipitate that is mechanically weak and easily dispersed in a wash solvent for ionic liquid extraction or drying.

The method has the following advantages: precipitating cellulose or biomass from an ionic liquid solution without encountering an intermediate gel phase greatly simplifies processing hardware required, requires less mixing time, requires less mixing energy, and produces a more desirable product (with respect to surface area) than results from the use of a single precipitating agent or mixture different from the one described here.

FIG. 3 shows the B+W plots of phase diagrams for the ethanol/acetone/EMIM Acetate/cellulose system. The area one should operate is designated as the "porous solid+liquid" region wherein a biomass precipitating solvent that does not form a gel phase.

Figure 4:
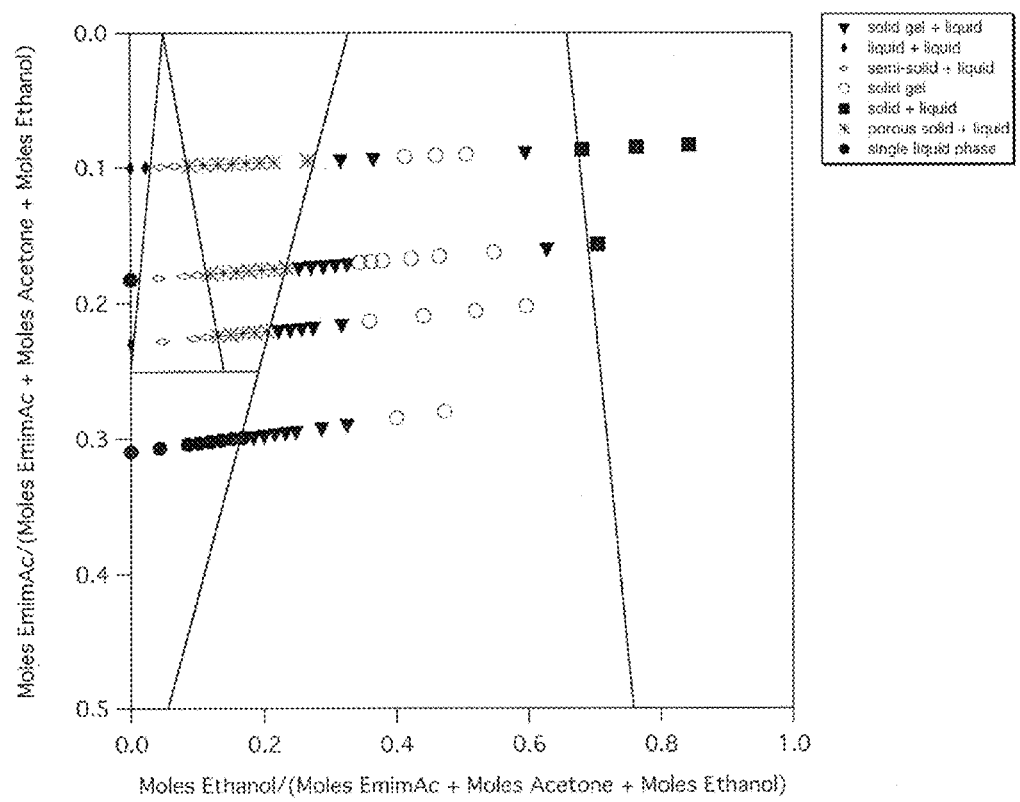
FIG. 4 shows the forms observed for the various solutions tested.

FIG. 4 shows the forms observed for the various solutions tested.

Figure 5:
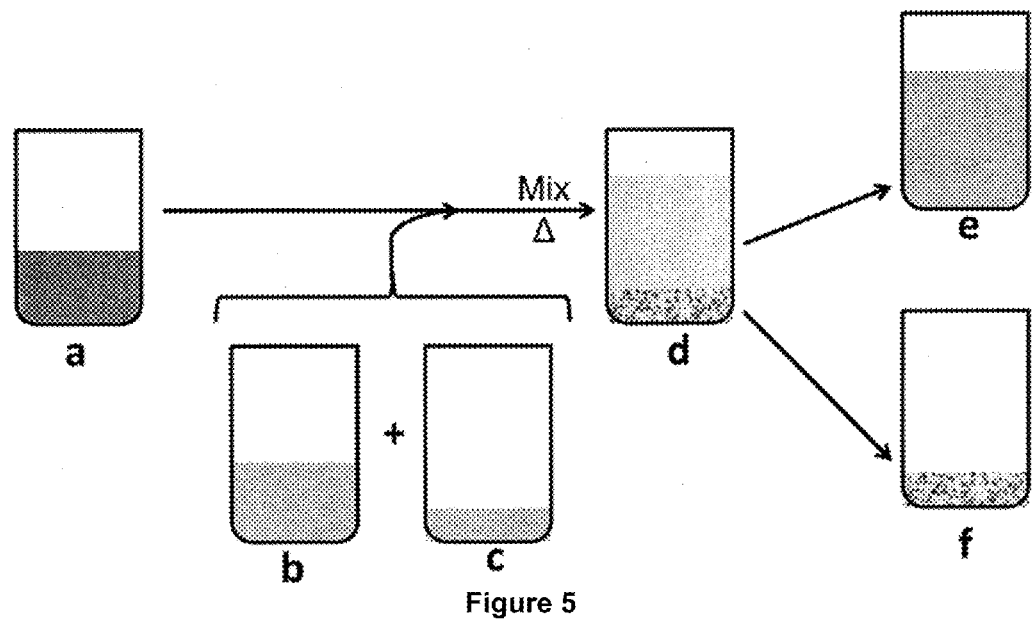
FIG. 5 shows a scheme for a precipitating agent mixture for recovering dry, amorphous, high surface area biomass from IL solutions without formation of a gel-phase intermediate "a" is an IL solution of cellulose biomass. "b" is a ketone portion of precipitating solvent. "c" is a alcohol portion of precipitating solvent. "d" is precipitated cellulose or biomass in IL/ketone/ethanol mixture. "e" is a liquid IL/ketone/alcohol fluid obtained from a liquid-solid separation process. "f" is wet solid that may be extracted, washed or any means processed to remove the remaining IL and then, optionally, dried.

FIG. 5 shows a scheme for a precipitating agent mixture for recovering dry, amorphous, high surface area biomass from IL solutions without formation of a gel-phase intermediate "a" is an IL solution of cellulose biomass. "a" can be 1-25% w/w. In some embodiments, "a" is 5-15% w/w. "b" is a ketone portion of precipitating solvent, such as acetone, methyl ethyl ketone, or the like. The ketone can be more than 3 moles ketones/mole IL cation. In some embodiments, the ketone is from 3 to 4 moles ketones/mole IL cation. "c" is an alcohol portion of precipitating solvent, such as methanol or ethanol. In some embodiments, the alcohol is from 0.8 to 1.1 mole alcohol/mole IL cation, or from 0.9 to 1.0 mole alcohol/mole IL cation. "d" is precipitated cellulose or biomass in IL/ketone/ethanol mixture. The precipitating material is formed by thoroughly mixing the system on addition of ketone and alcohol and is easily dispersed, mechanically weak porous solid or a floc or slurry depending on the original cellulose or biomass concentration in the IL. "e" is a liquid IL/ketone/alcohol fluid obtained from a liquid-solid separation process, such as filtration sedimentation, decantation, centrifugation, or the like. "f" is wet solid that may be extracted, washed or any means processed to remove the remaining IL. On drying, and if limited or no exposure to water has occurred, the dry solid has a high porosity and can exist as a powder or porous friable solid when dried.

EXAMPLE 3

Recovery of Dry, Amorphous, High Surface Area Biomass from Il Solutions without Formation of Gel-Phase Intermediate Describe herein is the phase-splitting behavior of hydrophilic ionic liquid/ketone mixtures on exposure to small quantities of hydrogen-bonding solvents such as water. In this example, this phenomenon is extended and apply it to separation of solutes such as biomass dissolved in ILs. Described herein is the phase splitting behavior of ketone-alcohol-ionic liquid-water system in the presence of substantial quantities of solutes. The solutes and controlled addition of weak hydrogen bonding solvents such as alcohols and organic acids modify the phase splitting reaction by making it much less sensitive to water addition, and by concentrating solutes in one of the newly produced liquid phases. By careful stepwise addition of phase-splitting solvent, different fractions of a second liquid phase can be produced, and the solutes in the original system fractionate into these different fractions based on their relative partitioning to the more or less hydrophilic liquid phase. An example of this behavior is provided: dissolving corn stover, a potential source of cellulosic biomass for fuel production, in an IL and generating three different product fractions: a bulk fraction that contains most of the biomass cellulose and high molecular weight lignins, a smaller fraction that has a relatively high content of water-soluble sugars, other carbohydrates, and lignin; and a third fraction containing hydrophobic substances such as, lipids, long chain alcohols, waxes, and other materials commonly referred to as "extractables". After separating these three fractions, the IL recovered is shown to be of a relatively high purity and suitable for re-use.

This invention provides a method of fractionating, concentrating, and for some cases isolating solutes and impurities dissolved in an ionic liquid. Various methods of chromatography may be able to accomplish many of the same results as the method described here, but only at great difficulty and expenditure of time and energy. The process is the only practical, scalable method for fractionating materials with a high affinity for the ionic liquid solvent. It may also be possible to separate miscible ionic liquids with this technique, even if they share the same counterion. This separation would be difficult or impossible using conventional techniques.

Figure 6:
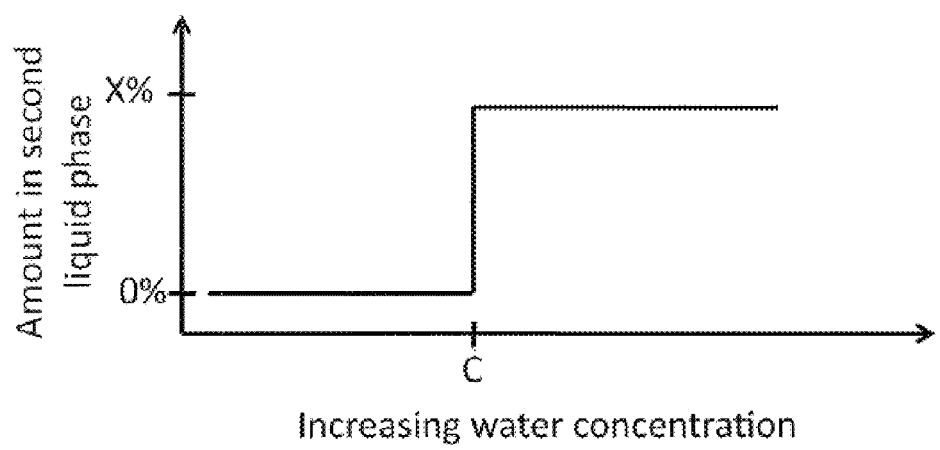
FIG. 6 shows the phase splitting of relatively pure IL/ketone/alcohol system on addition of hydrogen bond donor solvent such as water.

FIG. 6 shows the phase splitting of relatively pure IL/ketone/alcohol system on addition of hydrogen bond donor solvent such as water. In a system comprising hydrophilic IL (such as EMIM Acetate), a ketone, and water or other strong hydrogen bond donor/acceptor, there exists a sharp phase transition boundary at a critical water concentration, C, above which the single phase liquid solution splits into two immiscible phases and separate on standing. For light ketones, such as acetone, the IL-rich layer is denser and collects as a bottom layer. The solubility of at least one IL, such as EMIM Acetate, has a low solubility (less than 5% w/w) in the upper ketone layer, and that substantially all of the water is present in the lower IL-rich phase for water concentrations near the critical concentration. At the critical concentration of added water the ratio of the two liquid phases increases very sharply on addition of HBD (hydrogen-bond-donor) solvent. The amount of second phase produced (X %) is dependent on the ketone used, the IL used, and whether water or a different hydrogen bonding solvent is used.

Figure 7:
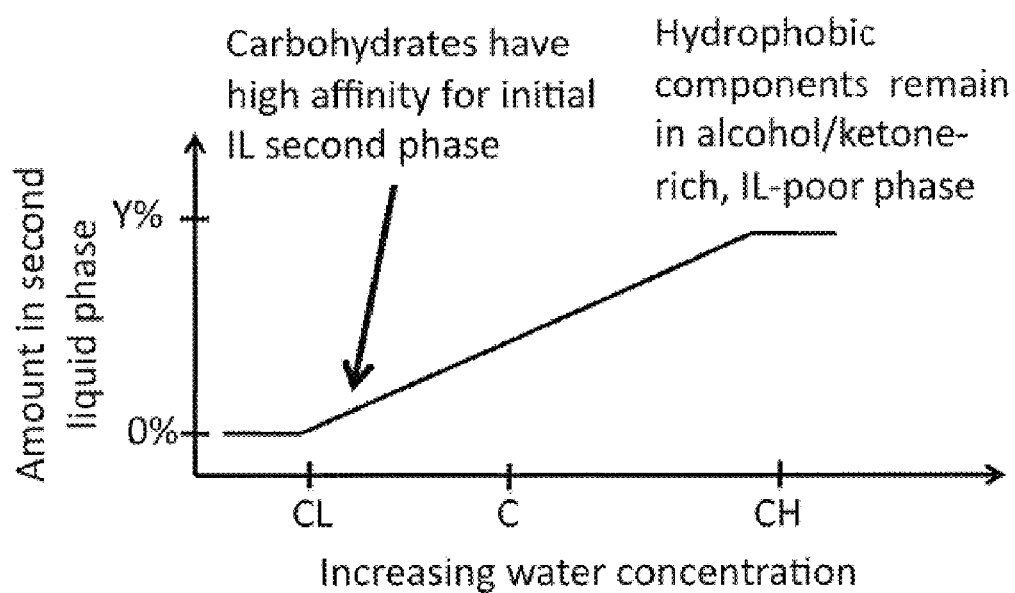
FIG. 7 shows the phase splitting of relatively pure IL/ketone/alcohol system with high solute content on addition of hydrogen bond donor solvent such as water.

FIG. 7 shows the phase splitting of relatively pure IL/ketone/alcohol system with high solute content on addition of hydrogen bond donor solvent such as water. When solutes are present in the same system as described for FIG. 6, the phase-switching behavior of the system is modified. The quantity of a second phase generated becomes less sensitive to the concentration of water or other hydrogen-bonding solvent. This allows some flexibility and control in the intentional generation of the phase splitting process. It is found that solutes preferentially segregate to one of the two generated phases, and the concentration of solutes within a generated phase can greatly exceed the original concentration of solutes in the original single phase solution. As such, it is found that a method of separating and concentration solutes by control of phase splitting behavior by addition of small quantities of water or other hydrogen bonding solvent.

In particular, it is found that the addition of a small amount of water to an acetone-EMIM Acetate mixture that contains both hydrophilic solutes derived from biomass (sugar and sugar oligomers and lignin) and hydrophobic solutes (hydrophobic plant extracts) can be separated and concentrated from their original mixed solution by careful control of solution water content or acetone/water ratio. This method works with additional ketones, such as methyl-ethyl ketone, diethyl ketone, cyclopentanone, cyclohexanone, and the like. Alcohols and other weak hydrogen bond donors, such as acetic acid, modify the behavior of the system by increasing the critical concentration of water necessary for phase splitting to occur and by changing the solvent properties of the liquid phases after phase splitting occurs. This allows additional fine control over the phase splitting and solute partitioning as may be desired. NMR analysis has confirmed that carbohydrate-rich and hydrophilic solutes and lignin separate out with the first generation of an IL-rich liquid phase, and with an excess addition of water to the solution mixture, hydrophobic substances that include aromatic and aliphatic compounds segregate to the ketone-rich/IL and water poor phase. The remaining IL that can be collected between these fractions contains only low levels of additional compounds, but even these could be concentrated and recovered by removing solute-rich phases as they are generated in as many fractions as desired. Thus, a method of selectively concentrating and fractionating solutes from a homogenous IL solution.

Figure 8:
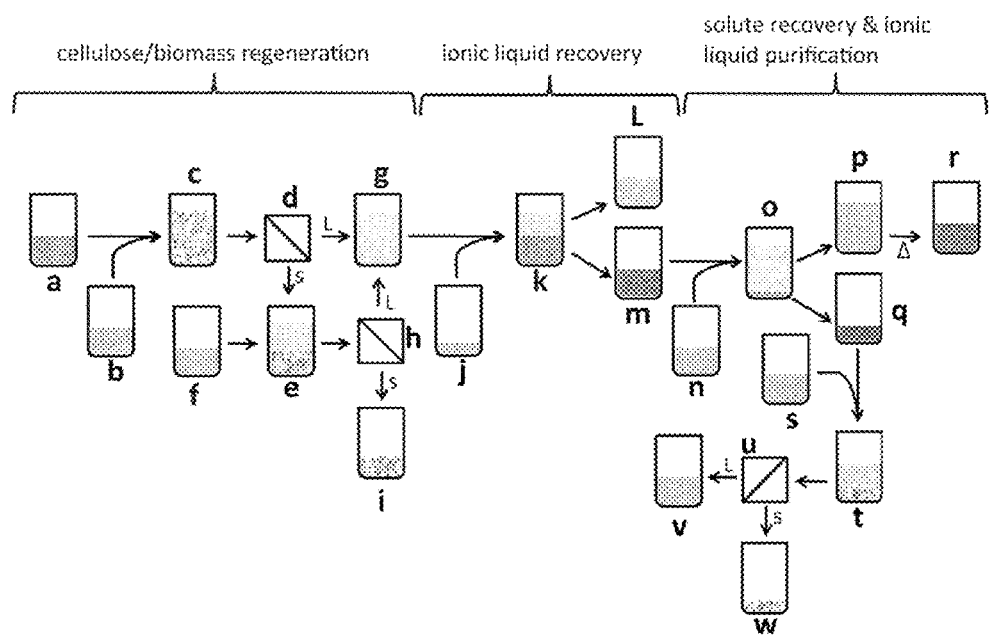
FIG. 8 shows the steps for an IL recovery process. "a" is a solution of biomass or cellulose in an IL. "b" is a precipitating solvent. "c" is a precipitated biomass produced by mixing "a" and "b" together. "d" is a liquid/solid separating system. "e" is a mixture of wash solvent and solids separated from "c" by processing in "d". "e" is a mixture of wash solvent and solids separated from "c" by processing "d". "f" is a wash solvent. "g" is a combination of precipitating solvent and wash solvents. "h" is a liquid/solid separation system. "i" is a solid product. "j" is a polar-protic phase-splitting solvent. "k" is a two-liquid phase solution produced by the addition of "j" to "g". "l" is a light (less dense, usually, rather than "light" depending on the ketone) fraction from the two phase system in "k". "m" is the heavy (more dense usually, but depends on solute and ketone used) fraction from the two phase system in "k". "n" is an alcohol or hydrogen-bonding solvent that causes a second liquid phase to form in the presence of solutes dissolved in "m". "o" is two liquid phases produced by the mixing of "m" and "n". "p" is the light (less dense) fraction from "o". "q" is the light (less dense) fraction from "o". "r" is the recovered IL obtained from "p" by evaporating or distilling off solvents at atmospheric or reduced pressure. "s" is a precipitating solvent. "t" is a solid/liquid two phase mixture produced by mixing "s" and "q". "u" is a solid/liquid separation system. "v" is a relatively pure IL dissolved in alcohol and some water. "w" is a solid recovered second product.

FIG. 8 shows the steps for an IL recovery process. "a" is a solution of biomass or cellulose in an IL. "a" can be 1-35% w/w. In some embodiments, "a" is 5-15% w/w. "b" is a precipitating solvent. The mixture of ketone and an alcohol is a desirable precipitating solvent that bypasses the formation of a gel-phase during biomass recovery and can be processed into a dry, high surface area product with desirable enzymatic hydrolysis characteristics. In some embodiments, this solution has a composition of about 1 mole-equivalent IL, 3-4 mole equivalent ketone, and 0.8-1.0 equivalent of an alcohol. "c" is a precipitated biomass produced by mixing "a" and "b" together. "d" is a liquid/solid separating system. "e" is a mixture of wash solvent and solids separated from "c" by processing in "d". "e" is a mixture of wash solvent and solids separated from "c" by processing "d". "f" is a wash solvent. This solvent or solvent mixture can be the same as the precipitating agent "b". A particularly useful solvent mixture is the azeotrope formed between acetone and methanol at atmospheric pressure (~12% w/w methanol in acetone). This mixture has a low boiling point and sufficient alcohol to handle moderate water absorption without the formation of a second liquid phase. "g" is a combination of precipitating solvent and wash solvents. Combination of these two solvent is not necessary, but offers the advantages for IL recovery if the wash solvent is the same or similar to the precipitating solvent. "h" is a liquid/solid separation system. "i" is a solid product. This is the primary process product (most the weight of biomass ends up in this fraction). The process of "f" to "h", washing and liquid/solid separation can be repeated as many times as needed for recovery of IL. "j" is a polar-protic phase-splitting solvent. Water and other solvents are suitable solvents for this application. "k" is a two-liquid phase solution produced by the addition of "j" to "g". For a pure ketone-IL mixture, as little as 0.5% w/w may induce phase separation. Greater quantities of alcohols or some other weak hydrogen bonding solvents, such as acetic acid, increase the amount of water or other phase-splitting solvent required. "l" is a light (less dense) fraction from the two phase system in "k". When using light ketones, such as acetone, methyl-ethyl ketone, or the like, this phase has a high relative concentration of hydrophobic compounds, such as lipids, waxes, long-chain alcohols, and the like. Increasing the amount of hydrophilic solvent "j" increases the separation efficiency of these hydrophobic compounds to "l". "m" is the heavy fraction from the two phase system in "k". The process of phase-splitting solvent "j" and separation to "k" and "l" can be repeated by utilizing small quantities for "j" and thereby obtaining multiple different fractions "L1'", "L2''", "L3'''", "m1'", "m2''", "m3'''", etc. For light ketones, "m" contains most of the IL and nearly all of the dissolved hydrophilic materials, such as carbohydrates and lignin, originally in "a". "n" is an alcohol or hydrogen-bonding solvent that causes a second liquid phase to form. For some ILs, this solvent may be the same as both the precipitating agent "b" and the wash solvent "f". With most of the ketone removed in fraction "l", there is a higher ratio of alcohol to IL formed even when "n" is a mixture of ketone and alcohol. The higher alcohol content can be adjusted to compensate for the water or other solvent "j" added previously, and control of the relative water/alcohol ratio allows additional liquid/liquid fractionation to occur if desired. "o" is two liquid phases produced by the mixing of "m" and "n". "p" is the light fraction from "o". For light ketones, this contains substantially pure IL dissolved in alcohol and ketone. Water content is low. "q" is the light fraction from "o". "r" is the recovered IL obtained from "p" by evaporating or distilling off solvents at atmospheric or reduced pressure. "s" is a precipitating solvent. Alcohols such as methanol or ethanol work well to precipitate carbohydrates because they have low carbohydrate solubility and are miscible with ILs. "t" is a solid/liquid two phase mixture produced by mixing "s" and "q". "u" is a solid/liquid separation system. "v" is a relatively pure IL dissolved in alcohol and some water. This liquid can be combined with "p" and recycled in the process. "w" is a solid recovered second product. The product is similar to "i" but may contain lower molecular weight carbohydrates, soluble tannins, lignin, IL-carbohydrate complexes, and the like.

Figure 9:
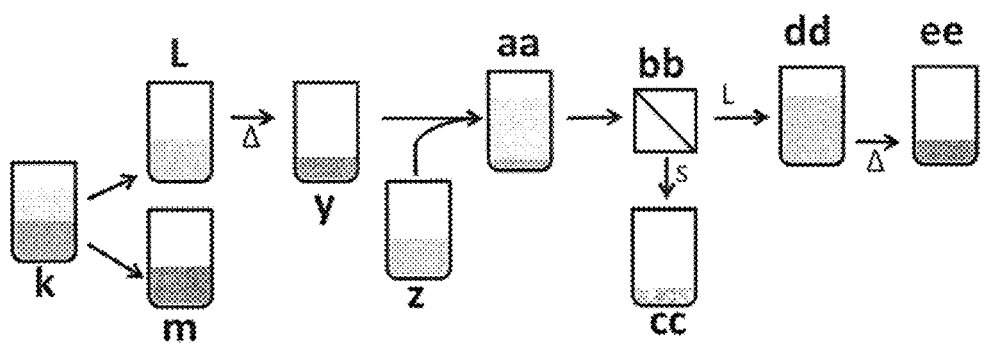
FIG. 9 shows a fractionation process for the light fraction recovered from "k" in FIG. 8. "L" is the light fraction from two phase mixture "k". "y" is the heating of "L" at atmospheric or reduced pressure to remove light ketones and leave a mixture of IL and hydrophobic substances. "z" is a polar protic precipitating solvent, such as water. "aa" is a solid/liquid two phase system formed by mixing "y" and "z". "bb" is a liquid/solid separation system. "cc" is a solid hydrophobic product. "dd" is a IL/precipitating solvent mixture. "ee" is a recovered pure IL. Hydrophobic substances can also be extracted by liquid-liquid extraction using a non-polar solvent and extracting "y" directly.

FIG. 9 shows a fraction process for the light fraction recovered from "k" in FIG. 8. "L" is the light fraction from two phase mixture "k". "y" is the heating of "L" at atmospheric or reduced pressure to remove light ketones and leave a mixture of IL and hydrophobic substances. "z" is a polar protic precipitating solvent, such as water. "aa" is a solid/liquid two phase system formed by mixing "y" and "z". "bb" is a liquid/solid separation system. "cc" is a solid hydrophobic product. When the biomass is derived from corn stover, this fraction is a tan, greasy solid. On melting it becomes a transparent brown sticky solid. "dd" is a IL/precipitating solvent mixture. "ee" is a recovered pure IL.

Figure 10:
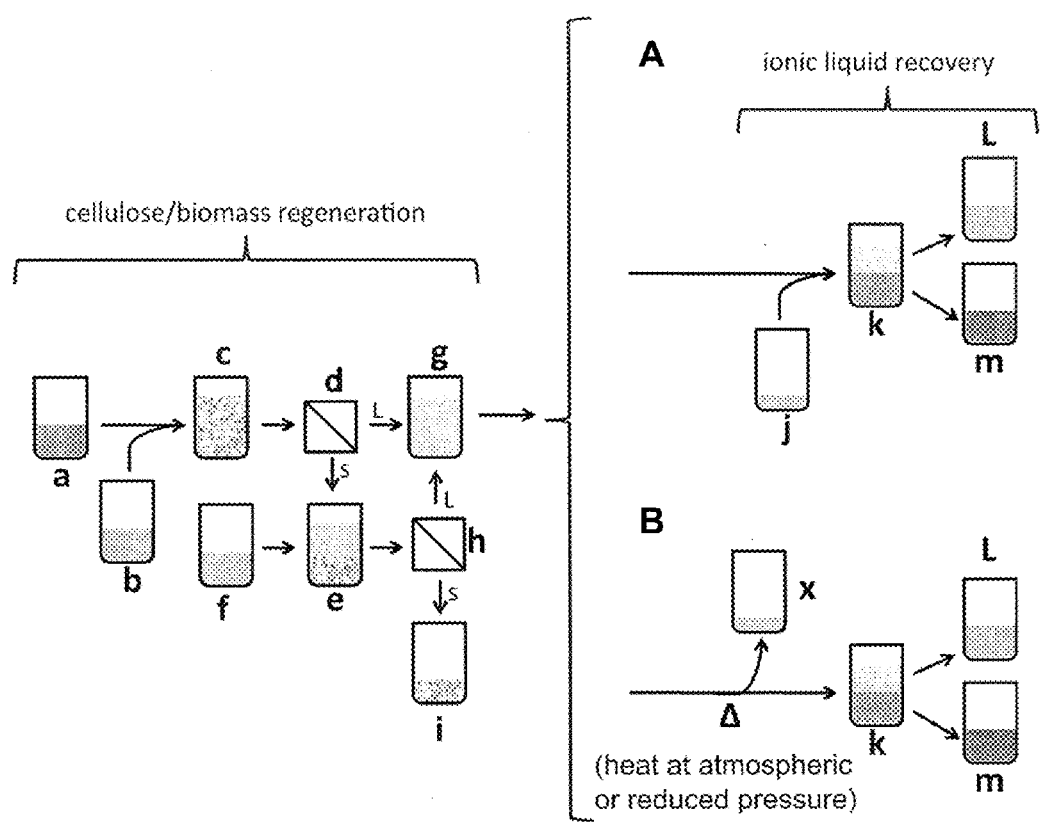
FIG. 10 shows the steps for two IL recovery processes. Panel A shows the steps as indicated in FIG. 8. Panel B shows an alternate method where a low boiling point alcohol and high boiling point ketone are used.

FIG. 10 shows the steps for two IL recovery processes. Panel A shows the steps as indicated in FIG. 8: a hydrogen-bonding phase splitting solvent, such as water is added to alcohol/ketone/Il mixture to induce phase splitting and separation. Panel B shows an alternate method where a low boiling point alcohol and high boiling point ketone are used for solutions "b" and/or "f" such as pentanone, or hexanone. On heating the mixture "g" at atmospheric or reduced pressure, the alcohol is removed first, resulting in the formation of two liquid phases. Fractionation of the mixture in "g" can be performed by regulating the amount of alcohol removed and therefore the amount of second liquid phase produced. This alternative method has the advantage of not requiring the addition of a polar protic solvent that is difficult to remove from the IL.

Figure 11:
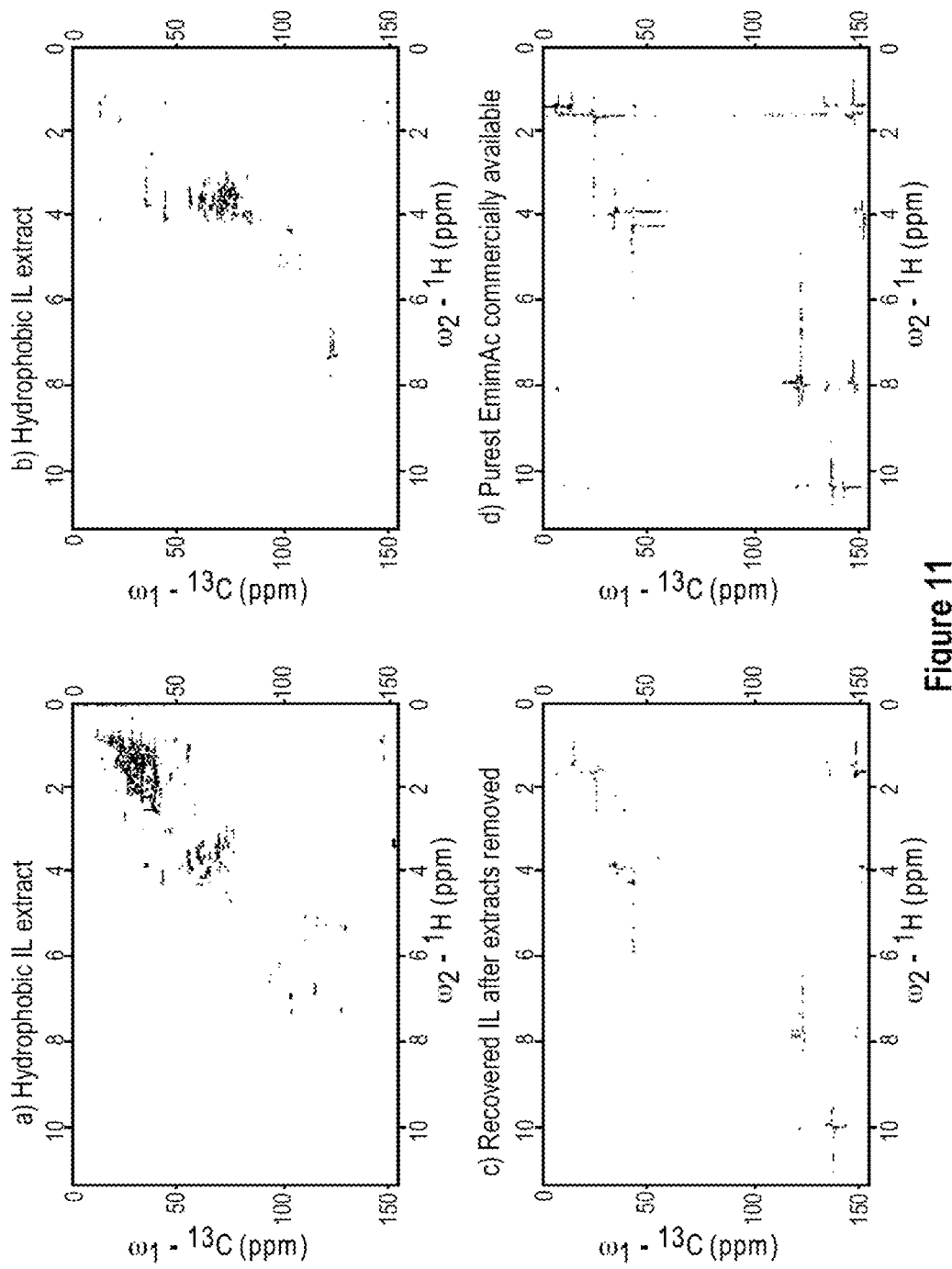
FIG. 11 shows the two-dimensional heteronuclear single quantum correlation nuclear magnetic resonance (HSQC NMR) spectra of compounds separated using the methods described herein.

FIG. 11 shows the two-dimensional heteronuclear single quantum correlation nuclear magnetic resonance (HSQC NMR) spectra of compound separated using the methods described herein. Panel a) shows the spectra for hydrophobic extract. This material is separated from IL used for processing corn stover and is the equivalent to "cc" in FIG. 9. Panel b) shows the spectra for water soluble hydrophilic extract. This is material separated from IL used to process corn stover and is equivalent to "w" in FIG. 8. Panel c) shows the spectra for IL after removal of hydrophilic and hydrophobic fractions "a" and "b". This is material equivalent to "r" in FIG. 8 after passing it through the hydrophilic extraction procedure described in FIG. 9. There are very few chemical linkages (only 2 identified) present that are not present in the original IL. Panel d) shows the spectra for a sample of the purest available grade of IL used for this test processing (EMIM Acetate). Based on the NMR spectra, the IL recovered after processing biomass and processed with the methods described herein has the same or less impurities than unused IL, although the color was darker for the used and recovered material.

EXAMPLE 4

Ionic Liquid Pretreatment with Gel-Free Precipitation and IL Recycling Utilizing a Phase-Switchable Solvent system The development of new sources of domestic, renewable, and carbon neutral liquid fuels is generally regarded as an urgent priority driven by multiple factors. Petroleum supplies are not increasing as fast as desirable, suggesting that higher costs for petroleum-derived products are likely in the future. Environmental concerns over continued fossil carbon emissions are driving a search for carbon-neutral energy sources. The high reliance of developed countries on imported petroleum impacts economic and political security on a global basis. One of the few options available for addressing these concerns is cellulosic biofuels'. Lignocellulosic biomass (LBM) is potentially available domestically in large quantities[2], and can be converted to biofuels in production processes that are (near) carbon neutral[3], and at costs competitive with petroleum[4]. Unfortunately, liquid fuel production from LBM currently requires expensive processing and additional technological developments are necessary for realization of biofuel production at volumes that impact current petroleum consumption significantly.

In the biochemical conversion of lignocellulosic biomass to fuels, the process of pretreatment is one of the most difficult and expensive operations. The use of ionic liquids (ILs), low melting point organic salts with novel solvent properties, in biomass pretreatment has received considerable attention recently because of their effectiveness at decreasing biomass recalcitrance to enzymatic hydrolysis and their potential for decreasing the need for corrosive or toxic chemicals and associated waste streams that can be generated by other pretreatment methods. In this article, we address two significant challenges to the realization of a practical IL pretreatment process. First, we describe a mixture containing specific proportions of a ketone and an alcohol that precipitates cellulose and lignocellulosic biomass from IL solutions without the formation of intermediate gel phases. Second, an IL recycling process is described for the recovery and fractionation of lignin and most residual IL solutes that minimizes energy and solvent use. These two techniques are demonstrated by the pretreatment of 100 g of corn stover and the recovery IL and separate fractions rich in glucans, xylans, lignin, and non-polar substances.

The development of new sources of domestic, renewable, and carbon neutral liquid fuels is generally regarded as an urgent priority driven by multiple factors. Petroleum supplies are not increasing as fast as desirable, suggesting that higher costs for petroleum-derived products are likely in the future. Environmental concerns over continued fossil carbon emissions are driving a search for carbon-neutral energy sources. The high reliance of developed countries on imported petroleum impacts economic and political security on a global basis. One of the few options available for addressing these concerns is cellulosic biofuels'. Lignocellulosic biomass (LBM) is potentially available domestically in large quantities[2], and can be converted to biofuels in production processes that are (near) carbon neutral[3], and at costs competitive with petroleum[4]. Unfortunately, liquid fuel production from LBM currently requires expensive processing and additional technological developments are necessary for realization of biofuel production at volumes that impact current petroleum consumption significantly.

In the process of transforming LBM into simple carbohydrates suitable for microbial fermentation to fuel or other chemicals, the operation of pretreatment that increases LBM susceptibility to enzymatic hydrolysis is perhaps the most difficult and expensive[5]. Several technologies for pretreating LBM have been investigated and described in various review articles[6-10]. A relatively new technology for pretreating LBM involves ionic liquids (ILs); molten salts composed of organic cations or anions with low melting points and unusual solvent properties[11-13].

Figure 12:
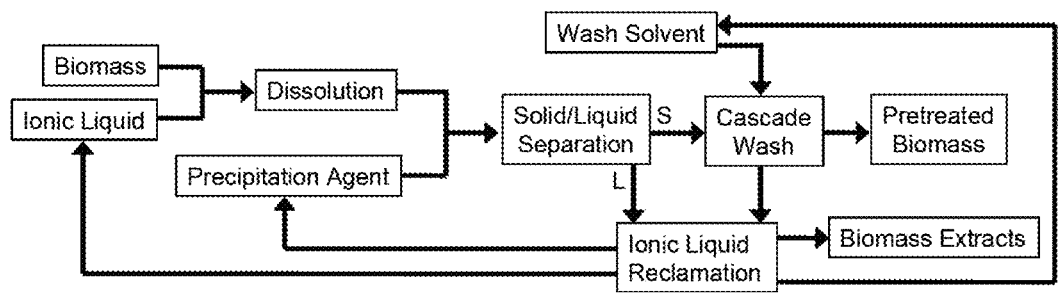
FIG. 12 shows a simplified diagram of an ionic liquid pretreatment process. The ionic liquid reclamation step is one of the most difficult and least studied aspects of this process.

IL pretreatment has been shown to reduce the crystallinity, hemicellulose and lignin content of LBM and increase its surface area, enzymatic hydrolysis kinetics, and yield of fermentable sugars.[14-18] IL pretreatment occurs at moderate temperature and ambient pressure and has been shown to result in low rates of carbohydrate degradation.[19,20] Certain ILs have been demonstrated to completely dissolve wood,[14,17,18,21-23] agricultural byproducts such as straw,[24] potential biofuel crops such as switchgrass,[16,17] and other biopolymers.[25-28] While investigators have proposed in situ hydrolysis of carbohydrate oligomers to monomers while dissolved in an IL with enzymes,[29] or acid catalysts,[30] or catalytic conversion of the carbohydrate components of LBM directly to potential fuel candidates,[31,32] a more typically described process involves a separate enzymatic conversion step following an IL pretreatment process as shown in FIG. 12.

In a typical IL pretreatment process, the ionic liquid and milled or ground, dried LBM are mixed and heated until some or all of the LBM has dissolved. Both water content and particle size of the initial LBM are important parameters, as water dramatically reduces the solubility of most LBM components in ILs, and dissolution rate and extent is increased with decreased LBM particle size.[21,33] A precipitating agent, typically water or an alcohol[15-17,20-24] is added to precipitate a fraction of the dissolved LBM, rich in glucan relative to the starting material. The precipitated glucan-rich product is washed to remove excess IL, and the combined precipitation and wash liquids are processed to recover the IL for recycling back into the process.

Recycling the IL and the efficient recovery and removal of residual LBM solutes in the used IL is a key step in an IL pretreatment process, and yet is one of the least described in the literature. With the expectation that ILs will be much more expensive than other materials involved in LBM pretreatment processing, recovery operations must have high yield and recycle the IL multiple times if the process is to become economically viable.[12,22,23,34] The recycling process should remove IL solutes that degrade process efficacy and be as simple and inexpensive as possible, requiring a minimum of additional or non-recycled reagents and cannot result in significant IL degradation. However, the separation of a mixture of carbohydrates, non-polar substances, low molecular weight lignin fragments, and other biomass components from ILs used for biomass pretreatment is a recognized challenge[12,18,22,23] that is in many ways more difficult than the precipitation of high molecular weight cellulose, xylans, and lignin because of intrinsically higher solubilities that accompany reduced molecular weight of these solutes. If water is used as the precipitation or wash solvent, then the situation is even more challenging because of the high solubility of monomer and small oligimer carbohydrates in water. The IL recycling process is further challenged if acids or other homogenous catalysts are used in the IL for carbohydrate depolymerization or conversion of LBM carbohydrates directly to fuel molecules.

A few solutions to the problem of IL recycling have been proposed in the literature. Some of the lignin that remains in the IL can be precipitated by the addition of an acid or evaporation of a water+acetone mixture containing the used IL.[18] Liquid phase separations are among the lower cost and complexity options, and a few biphasic IL systems have been proposed. Concentrated salts[35,36] for example can induce phase separation in aqueous IL solutions, but may not be selective enough for practical applications.[12] Phenylboronic acid and other boronates have been shown to form extractable complexes with carbohydrates from IL-water solutions.[37] Polar solvents such as acetonitrile or dichloromethane;[14] nonpolar solvents such as ether,[38] and ethyl acetate,[39] and polymers such as polyethylene glycol[40,41] form immiscible phases with polar ILs and can be used to extract or separate some biomass components from IL solutions. Depending on the type and concentration of biomass solutes remaining after these procedures, IL have in some instances been recycled multiple times.[22,39,42] However, all of the proposed methods present challenges when considered as part of a practical, large-scale biomass pretreatment process because of high cost, complexity, excessive solvent requirements, or limited effectiveness at removing sufficient solutes for IL recycling while maintaining nearly complete recovery of the process IL.

Most reports in the literature on IL pretreatment utilize low substrate loadings of 3-5% (w/w) biomass in IL[14,16-18,21,23,24,38,42] and large quantities of precipitating solvent (i.e. 10:1 v/v precipitation solvent to IL).[18] A practical IL pretreatment process must maximize the substrate concentration and throughput, and utilize a minimum quantity of precipitation and wash solvents while still recovering a very large majority of the IL used for processing. However, at high substrate loadings IL solutions of LBM can have very high viscosities, and precipitation of LBM from an IL solution with water or alcohols can result in gel phases that greatly complicate physical separation of precipitated solutes from the IL. The formation of these gel-phases occurs with water or alcohols at LBM loadings as low as 3 wt %[43] and has several consequences. Mixing gel phases, which can be quite stiff mechanically relative to the already very viscous IL solution, can be very difficult, even in the presence of an excess solvent. If the gel phase is not completely dispersed in additional solvent, the quantity of IL entrained in the solid glucan-rich precipitate can be high, resulting in loss of the expensive IL and potentially increased toxicity to downstream process organisms.

In this article we describe two advances facilitating the practical realization of an IL LBM pretreatment process: the elimination of gel phases during precipitation of a glucan-rich biomass fraction, and the extraction and recovery of residual IL solutes that leaves the IL with sufficient purity for recycling back into the process in high yield. Both of these processes utilize only acetone and light alcohols, facilitating their integration into a complete process with low energy requirements.

We describe a precipitation solvent mixture that precipitates cellulose or LBM from an IL without the formation of gel phases, at biomass concentrations up to at least 10% (w/w). Relative to water or neat alcohols, the solvent mixtures we describe reduces the quantity of solvent required for precipitation, requires less energy to separate from the ionic liquid, and eliminates higher viscosity transition periods during precipitation of glucan-rich biomass product fractions. Elimination of gel-phase intermediates also has the benefit of reducing the amount of IL entrained in precipitated solids, and its associated impact on down-stream processes and IL make-up expense.

We utilize a similar solvent system for recycling the IL by removing residual solutes that would otherwise accumulate during process cycles. The solvent system, containing acetone, 2-propanol, and a small amount of water, forms a switchable, biphasic liquid process that concentrates and provides a means to separate oleophillic solutes, short chain carbohydrates, and lignin fragments from used ionic liquid in a two stage extraction procedure. The process is demonstrated by pretreating corn stover at the 100 g scale, at 10% (w/w) loading in IL, recovering the IL with low residual solute levels, and by characterizing the mass balances, recovered products, saccharificaton performance, and residual IL in the glucan-rich product fraction.

Results and Discussion
Gel-Free Cellulose and Biomass Precipitation

Figure 13:
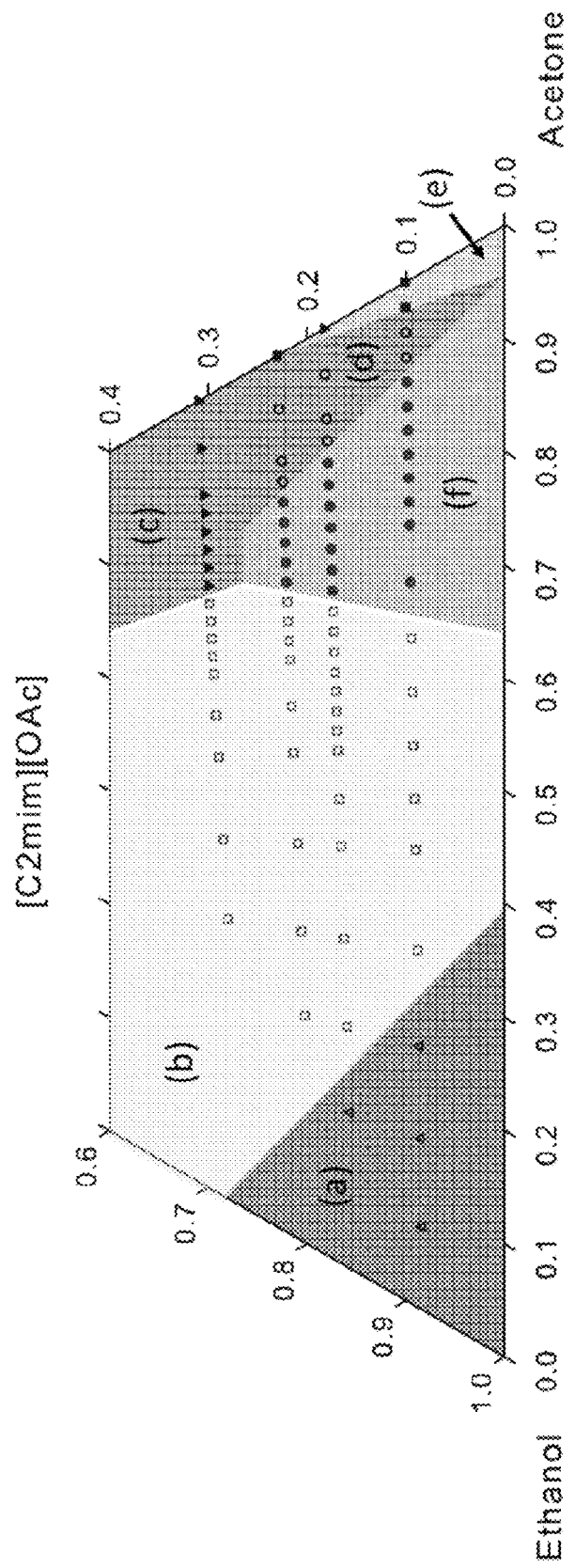
FIG. 13 shows the physical characteristics of cellulose precipitated from IL solutions as a function of solvent composition and quantity. Precipitated cellulose has the following characteristics: (a) compact solid+liquid; (b) gel phase present; (c) single liquid phase; (d) semi-solid or mixture of solid and viscous liquid; (e) two liquid phases; (f) loose solid+liquid. Precipitation in region (f) is desirable to avoid gel formation, for efficient mixing and liquid/solid separations, and for producing material with rapid enzymatic hydrolysis rates. [C2mim] [OAc] is the ionic liquid 1-ethyl-3-methylimidazolium acetate. Plot axis have units of mole fraction. Markers correspond to individual experiments; regions are estimated from data and are drawn as a guide only.

The formation of gel phases by the precipitation of dissolved cellulose or biomass has been reported in several contexts.[43-45] Preventing gel formation during LBM pretreatment is desirable because it decreases the energy and mechanical torque requirements for mixing and the difficulty of separating IL from solid products. While investigating the formation of gel phases from IL solutions as a function of precipitation solvent, we found that it was possible to regenerate cellulose without forming gel-phase intermediates if the precipitation solvent was a mixture of a ketone and alcohol within a specific composition range. FIG. 13 is a plot of the physical characteristics of cellulose precipitated from a 3.7% solution in [C2mim][OAc] as a function of precipitation solvent composition and concentration for mixtures of ethanol and acetone.

At high ethanol concentrations encompassed by region (a) in FIG. 13, precipitated cellulose is dense and mechanically tough. When using neat alcohols or water as precipitation solvents, mixing must be very rapid to avoid the formation of barrier films of precipitated cellulose between precipitation solvent and unprecipitated cellulose solution. To transition from an IL rich solution to the mixture of liquid and solid seen in region (a), the solution must pass through compositions within region (b) and form a gel phase. Alternatively, utilizing a precipitation solvent rich in acetone, but also containing some ethanol, the transition from IL rich solution to precipitated solids and free liquid can avoid formation of gel phases by passing through region (c), a single phase liquid, directly into region (f). Solids precipitated in region (f) appear porous and are mechanically very weak, facilitating mixing and rapid filtration during later washing operations utilizing either filtration or centrifugation. If too little alcohol is present in the precipitation mixture, (region (d)), the precipitated material is a semi-solid, or a mixture of solids and viscous liquid. Pure acetone or acetone with very low concentrations of alcohol (region (e)) do not appear to be effective at precipitating cellulose from [C2mim][OAc] solutions in our experiments and form a second liquid phase.

The useful composition range for solvents that will precipitate cellulose with the desirable characteristics found in region (f), can be expressed as a molar ratio X:Y:Z::Acetone: Ethanol:[C2mim][OAc], with $X>3$, $0.8<Y<1.2$, and $Z=1$ for normalization. In practice, inhomogeneities during mixing, high viscosities of both the IL solution and the slurry of precipitated materials, and minimizing solvent use to allow increases in process scale restrict the useful composition range of the precipitation solvent to approximately $3.3 \leq X \leq 8$, $Y \approx 1$, and $Z=1$ as before. In our 1-liter experiments with moderate cellulose and biomass IL concentrations in [C2mim][OAc] of 8-15%, $4 \leq X \leq 6$, $Y=1$, and $Z=1$ produces very good results and manageable viscosities. This was demonstrated precipitating cellulose from a 15 weight-% cellulose solution in [C2mim] [OAc] using a mixture of acetone and methanol with $X=3.3$, $Y=1$, and $Z=1$ to produce a powdery precipitate, that could be separated by filtration in less than 5 minutes. This precipitation solvent volume was approximately 1.7 times that of the IL solution, considerably less than the 3×-10× IL volume of precipitation solvent typically reported in the literature.[16,18] No gel phases formed during precipitation.

In FIG. 13 it can be seen that the minimum solvent concentration that precipitates cellulose is approximately the same in regions (a) and (f). However, the practical difficulties of mixing and dispersing gel phases into enough solvent to maximize liquid/solid separation in region (a) limit the minimum volume ratio of alcohol to IL solution to higher values than for region (f) unless cellulose solutions in IL are dilute and mixing of precipitation solvent and IL solution is very rapid.

It is easier to see gel formation in the precipitation of pure cellulose from an IL solution than for LBM such as CS, possibly because of the presence of lignin. However, the difficulty of completely separating liquid and solids when gel phases are present also impacts the efficient separation of IL from precipitated solids. The previously mentioned potential for neat alcohols and water to form barrier films around IL-rich regions of cellulose during precipitation also contribute to an increase in IL content. Unfortunately, IL content in pretreated biomass is not usually reported in the literature, and may not be recognized as significant until the pretreated materials are utilized as a biological growth medium or an effort is made to reduce precipitation and wash solvent quantities used during processing. For the development of a practical LBM pretreatment process, reducing the residual IL content in pretreated products by avoiding formation of gel phases and through washing or some other method is important because of the high cost of ILs and their potential for reducing hydrolysis or fermentation yields. In our experiments with CS, we were able to avoid the formation of gel phases during precipitation through the use of ketone and alcohol compositions bound by region (f) of FIG. 13, and found that with sufficient washing IL content could be reduced to less than 0.2%. However, the large quantities of liquids used for washing present challenges for IL recycling and suggest that optimization of this step is needed, preferably in a process that does not include water as a component.

Recovery of IL Solutes

Hydrophillic ILs interact strongly with water, and this interaction can be used to drive separation processes. The strong interaction of water with ILs is primarily governed by the IL anion[46,47] and decrease the IL polarity.[48,49] The interaction strength of [C2mim] [OAc] when is quite strong, as indicated by a report[50] of 11 KJ/mole being necessary to remove the most tightly bound water and the formation of a [C2mim][OAc].12H$_2$O complex. Several studies suggest utilizing this strong interaction for the separation of water and alcohol mixtures and the elimination of azeotropes.[51,52] We propose utilizing the strong interaction of water and other hydrogen bond donor solvents with hydrophilic ILs to drive phase separation and biomass fractionation as shown in FIG. 14.

Figure 14:
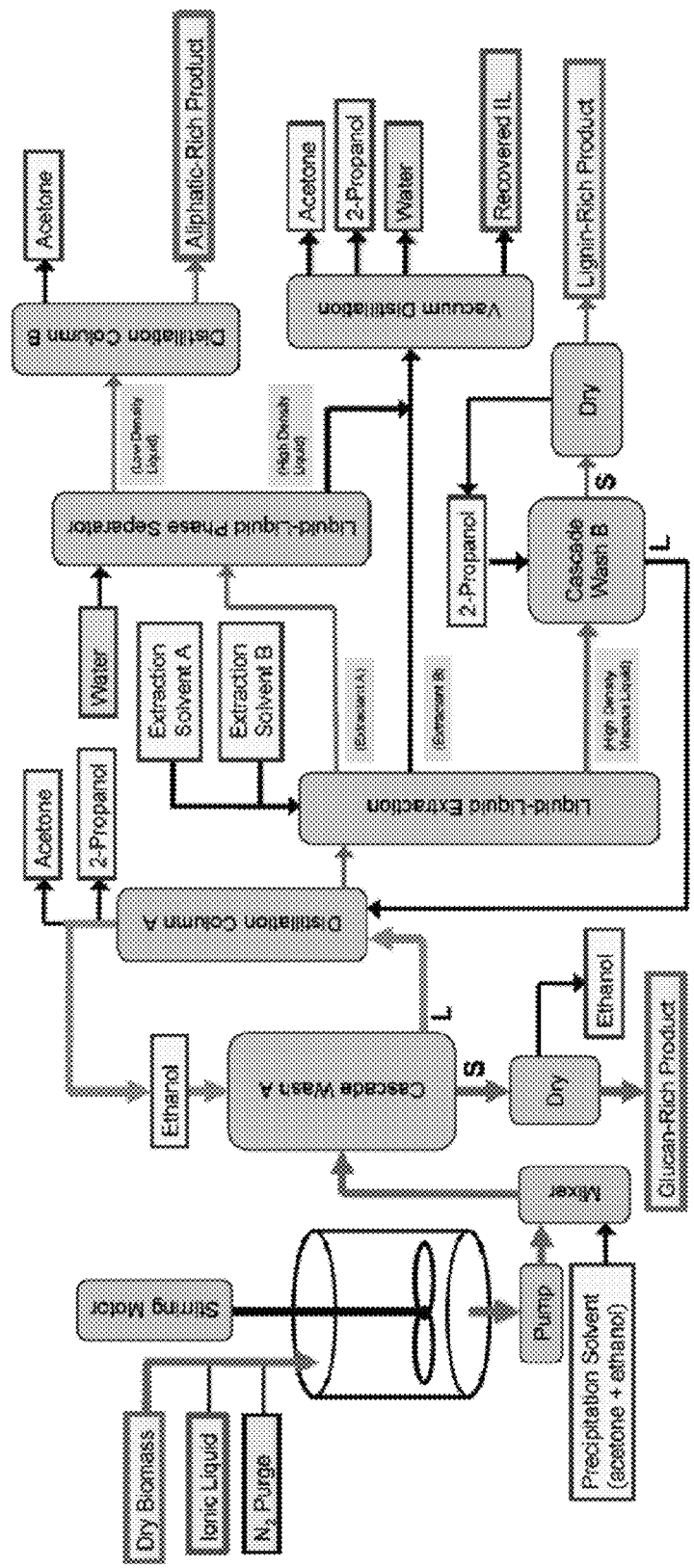
FIG. 14 shows the proposed ionic liquid (IL) pretreatment system with gel-free biomass precipitation and recovery of solutes from used IL. Extractant A is dry acetone. Extractant B is a mixture of acetone and 2-propanol with variable composition (see Example 4). S=Solid, L=Liquid. Recovered IL can be reused in this process without further purification.

There are four basic operations in our proposed IL recycling process depicted in FIG. 14. They are: A) distillation of the combined precipitation and wash solvents, B) extraction of non-polar substances from the IL, C) concentration of IL solutes by the extraction of IL and water, and D) precipitation and reduction of IL content in the recovered solutes by washing. The separate products of the final three operations are then 'dried' by thermal removal of undesired water or solvents. A key aspect of this process is the adjustable solubility of [C2mim][OAc] in acetone through the use of water or alcohols.

Dry acetone (<0.1% H$_2$O) and [C2mim][OAc] (<0.3% H$_2$O) are miscible, but acetone containing only 1% water reduces [C2mim][OAc] solubility to less than 0.05%. This level of water is rapidly picked up by either the IL or by solvents on atmospheric exposure. Ethanol and other alcohols are good co-solvents for this system, restoring the solution to a single-phase state when added in similar quantities to the amount of water present. This phase-switchable quaternary system of IL-water-ketone-alcohol provides a very sensitive and convenient means of controlling separations, and may be a general property of hydrophilic ILs. Cyclic and acyclic ketones with 3-6 carbon atoms and alcohols with 1-4 carbon atoms also demonstrate this behavior with only minor differences (data not shown). 1-ethyl-3-methylimidazolium chloride [C2mim] [Cl] also has similar behavior, at least for the higher molecular weight ketones with boiling points above the 79° C. melting point of [C2mim] [Cl] (data not shown). We have titrated water and ethanol against each other to repeatedly alternate between a single and two-phase system to ethanol concentrations greater than 20% by weight in the [C2mim] [OAc] system, demonstrating the flexibility of this switchable solvent system over a range compositions.

Referring to FIG. 14, alcohols present in the combined precipitation and wash liquids maintain the IL solution in a single-phase, and must be removed prior to recovery of other IL solutes. Distillation is the initial step in the IL recovery process and is needed to remove acetone and alcohols from the IL but can leave water with the IL to induce a phase separation that is required in the next process step. The recycling of precipitation and wash solvents by distillation from the ionic liquid, colored orange in FIG. 14, may be the most energy intensive operation in our proposed pretreatment process because of the large solvent volumes encountered that are required for maximizing recovery of the expensive IL.

With the alcohols removed by distillation, the addition of acetone causes the IL solution to form a second phase that facilitates extraction of non-polar substances with additional acetone. NMR analysis of this extract, the aliphatic-rich product in FIG. 14, suggests that it contains relatively low quantities of aromatics relative to saturated hydrocarbons (data not shown). Addition of water to the acetone extract results in the nearly complete removal of residual IL to a higher density second liquid phase but leaves non-polar substances in the upper, acetone-rich phase.

The solutes remaining in the IL are concentrated by extracting the IL with acetone containing a few percent alcohol, the alcohol increasing the solubility of the IL, water, and solutes in the upper acetone phase, but to a different degree. 2-propanol was chosen for its low polarity and thus low solubility for sugars[53] and acetone insoluble substances remaining in the IL. The 2-propanol concentration necessary in the acetone extraction solvent is dependant on the water content in the IL, influenced by the water content of the biomass prior to pretreatment, the solvents used for precipitation and washing, and the conditions used for distillation of the IL. There is a trade-off between alcohol concentration and lignin recovery, with low alcohol concentrations favoring better separation of IL and the IL solutes. Ultimately, the purity requirement for the successful recycling of IL determine the quantities and number of extraction stages utilizing acetone and alcohol in this extraction and set a practical limit on the amount of water that can be left in the IL after distillation of the precipitation and wash solvents. Optimizing these quantities requires consideration and balancing of the economic aspects of several unit operations in the recovery process. 2-propanol could be used to replace the ethanol used in precipitation and wash stages to reduce the number of solvents from 3 to 2, at a somewhat higher energy requirement for recovery by distillation. Ethanol, however, is too polar to replace 2-propanol in the separation of lignin and other solutes from [C2mim] [OAc] and results in very low yield of recovered materials.

The viscous liquid remaining after extraction typically contains significant amounts of IL. Addition of 2-propanol precipitates a solid product, but the partial solubility of this product in 2-propanol meant that several processing stages were required to maximize recovered solids while maintaining a low residual IL content of the solid products. Compounds remaining in the IL whose concentration could increase with IL reuse must possess a combination of low solubility in acetone and high solubility in dilute solutions of [C2mim][OAc], 2-propanol, and water in acetone.

From our description of the process in FIG. 14 it can be seen that the sensitivity of [C2mim][OAc] to water concentration impacts the entire pretreatment process in a complex and interrelated manner. The water content of a feedstock prior to pretreatment is known to impact its IL solubility, and therefore its enzymatic digestibility once pretreated at a given temperature. Both water content and alcohol type used as components of precipitation and wash solvents modify the distribution of carbohydrate and lignin fragments between the glucan-rich product and the IL prior to recycling, and thus also potentially influence the enzymatic digestibility or the concentration of microbial inhibitors in the glucan-rich product. The content of solutes, water, and alcohol present in the IL impact the product of the first IL distillation step, and so on. Overall, it appears desirable to minimize water content in the entire process, but this must be weighed against the process economics of drying the incoming biomass and solvents recycled during processing.

Fractionation is a desirable feature in biomass pretreatment as it offers the potential for isolation of higher value products from biomass. There are many opportunities for fractionating biomass components in the process we have described based on their polarity or solubility in the process solvents and utilizing the sensitivity of the phase splitting behavior of [C2mim][OAc]+acetone solutions.

Characteristics of Recovered Corn Stover Fractions and IL

Three products are obtained from the process described in FIG. 14, with a fourth product obtained in our experiments from the water wash of one of the initial three products. Table 1 contains a table with characteristics of the main chemical components of CS that are fractionated among these four products, and additional details of the chemical compositions of these products are provided in Table 2.

during pretreatment. CS in the glucan-rich product was recovered with a smaller particle size than the initial CS and presumably contained a different lignin distribution than present in the unpretreated CS because of the complete dissolution in IL. Because of the extensive washing used, the glucan-rich product contained less than 0.2% residual IL on a dry basis. Additional information on the enzymatic hydrolysis, IL content, composition, and images of CS before and after IL pretreatment is available in the supplementary information. Components of CS that did not dissolve in the IL, including insoluble inorganics and soil were captured by filtration and are included in this product fraction.

After an ethanol wash regimen, the glucan-rich product contained 2.7% (w/w) IL, a level too high for use in our fermentation experiments. Water washing removed most of the residual IL, along with 34% of the lignin present in the glucan-rich product and an unknown quantity of hemicellulose. Reducing the water wash liquids formed the xylan rich product, but was very energy intensive and is undesirable from a process standpoint. Developing a wash procedure or other operation that minimizes solvent and water use while removing the overwhelming majority of IL from pretreated solids remains a significant hurdle to the implementation of a scaled or economically viable IL pretreatment process.

Eliminating water as a wash solvent would also permit drying the pretreated solids to remove the wash solvent as suggested in FIG. 14, an operation that is much more difficult with water-wet LBM because of a reduction in surface area, pore collapse, and reduced enzymatic hydrolysis yield that result from a process known as 'hornification'.[54,55] Hemicellulose and free sugars have low solubility in most alcohols and leaving these with the precipitated biomass reduces hornification on drying,[56] increases the yield of recovered carbohydrates, and preserve a high enzymatic digestibility of the pretreated product (data not shown). A dry product at the end of pretreatment is advantageous because it permits arbitrary solids loading or fed-batch operations in downstream saccharification and fermentation operations and partially decouples pretreatment from downstream operations both physically (location) and chemically. We found that the impact of drying was dependant on the method used, and that vacuum drying from an ethanol-wet state resulted in an easily digestible product. Drying from a water-wet state, in either an atmospheric or vacuum oven reduced the digestibility,

TABLE 1

Recovery yields of the primary chemical constituents of corn stover after ionic liquid pretreatment.

| Recovered CS Fraction | Recovered Quantity, g (% of initial component) | | | | | |
|---|---|---|---|---|---|---|
| | Glucan | Xylan | Arabinan | Lignin | EtOH Extractives | Unidentified |
| Glucan-rich product | 29 (87) | 16 (64) | 3.1 (81) | 6.0 (35) | 0 | 9.7 |
| Xylan-rich product | — | — | — | 2.8 (17) | 0 | 12 |
| Lignin-rich product | — | — | — | 1.0 (5.9) | — | 1.7 |
| Aliphatic-rich product | — | — | — | — | 1.6 (48) | 0 |
| Total recovered | 29 (87) | 16 (64) | 3.1 (81) | 9.8 (58) | 1.6 (48) | 23 |

82.9 g total solids recovered (82.8% of initial dry mass)

The glucan-rich product is has a lignin content 45% lower than the unpretreated CS and is easily hydrolyzed with commercial enzymes, producing a reducing sugar concentration over 100% on an initial glucan basis without added xylanase in 48 hours utilizing a relatively low cellulase loading of 3.5 FPU/g. An absence of recognizable plant fiber in the regenerated product suggest that the CS was completely dissolved although freeze-drying could remove water without significantly impacting saccharification performance. Our observations are consistent with results reported on the preparation of high surface area cellulose aerogels or foams by regeneration from a solvent solution, in that drying from a solvent solution, solvent displacement, or freeze drying is needed to prevent poor collapse and an increase in density during drying.

The lignin-rich product recovered during IL has different solubility characteristics than native lignin. It has a high solubility in water and alcohol, suggesting extensive chemical modification or decrease in molecular weight result from IL pretreatment. The aliphatic-rich product obtained from the acetone extraction of [C2mim][OAc] in the recycling process is insoluble in water, but is mostly soluble in hexane. The chemical composition of this greasy, brown, semisolid product is unclear, but $^1$H NMR suggests substantial amounts of aliphatic hydrocarbons are present (data not shown), consistent with the complex mixture of fatty acids, long-chain aliphatic alcohols, sterols, terpenes, aromatics, triglycerides, waxes, and protein present in the alcohol extracts of many plants.[58,59] It has been shown that approximately half of ethanol extractives from CS measure as Klason lignin using standard testing protocols,[60] but further fractionation of this IL extract may provide a source of higher value plant lipids different from condensed polymeric 'lignin' that can result from more severe pretreatment processes or lignin quantification protocols utilizing acids at high temperatures. These substances may be desirable from a biorefinery perspective as a an additional high-value product stream and source for plant extractives.

Figure 15:
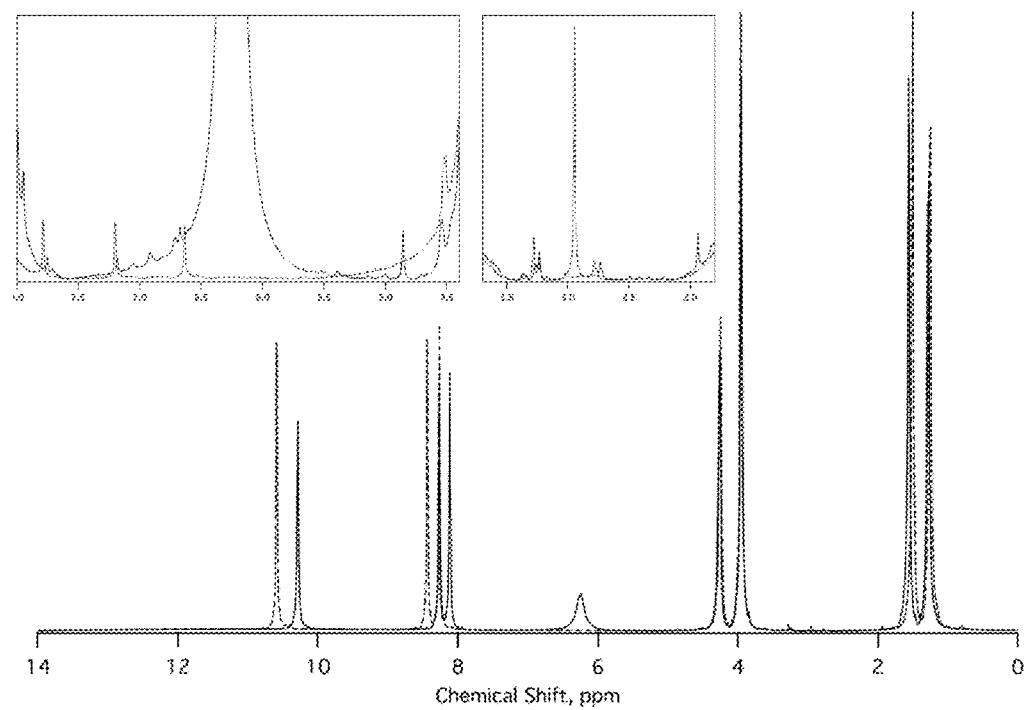
FIG. 15 shows the $^1$H NMR spectra of the IL 1-ethyl-3-methylimidazolium acetate prior to use (dashed) and after recycling as described in the text (solid). The primary impurity of the recycled IL is water. Many of the minor impurities present in the unused IL are removed in the recycling process.

The ionic liquid recovered from the recycling process we have described is much darker in color and contains different contaminants than the IL prior to use. The $^1$H NMR spectra of [C2mim][OAc] prior to use and after recovery is shown in FIG. 15. A table of chemical shifts for the as-received and recycled IL is available in the supplementary information. While $^1$H NMR typically has a sensitivity of approximately 1%,[61] both the as-received and recycled IL have impurity concentrations near this level and impurity peaks can be easily detected with our equipment. After recycling, all of the original impurities present in the IL are either not detected or are at greatly reduced levels. Many new impurity peaks are present in the IL spectra, in regions consistent with both carbohydrates and lignin. The dominant impurity in our recycled IL is water. It is possible to remove water from [C2mim][OAc] by vacuum distillation,[62] but apparently not at the rough vacuum levels available at our vacuum oven (base pressure approximately 100 mbar). The water content of the recycled IL shifts the IL spectral positions relative to the dry (<0.2% water specified) as-received IL and shows up as a relatively broad peak at $\delta_H$ 6.25 ppm. As mentioned previously, the impurity content (other than water) of IL recycled in our process is influenced by the water content and extraction conditions used during recycling, and these parameters were not optimized for maximizing IL purity in our experiments.

The work by Sun, et. al.[18] may contain the most comparable experimental data to what we present here. In their work, [C2mim][OAc] was used to treat pine and oak powders and some lignin was recovered through the use of an acetone+water precipitation and wash solvent system. Evaporating the acetone from the recovered liquids and adding acid each led to the recovery of a portion of the lignin contained in the original biomass. Relative to their work we have used 2× higher biomass loading in the IL, processed for <⅕$^{th}$ the time, used <¼ the precipitation solvent volume, and recovered considerably higher total carbohydrates (>77.4% vs. 59%). The fraction of lignin we recover is less that that recovered by Sun, et. al. (58% vs. 69%), however we have also collected a separate fraction rich in saturated hydrocarbons and characterized the IL content of all of our extracts, which was not in the previous study and could lead to overestimates of recovered mass. On a total solids basis, we recovered 83% of the initial dry mass and 89% of the initial IL, vs. 62% solids and no IL recovery in the previous work. Additionally, no acid or other catalysts were used in the process that we describe, while Sun, et. al. acidified their IL to precipitate a fraction of the recovered lignin, a practice that they admit would pose a problem for further recycling of the IL. Finally, the process described by Sun, et. al. does not appear capable of removing carbohydrate monomers and short oligomers from the IL solution, and these substances can account for more than 5% of the dry weight of biomass such as switchgrass,[63] while the process we have described removes essentially all carbohydrates from [C2mim][OAc] because of their low solubility in organic solvents such as acetone and light alcohols. This is an important consideration for the recycling of ILs in a practical pretreatment process.

The IL-ketone-alcohol-water phase-splitting process we have described for concentration or fractionation of biomass solutes from [C2mim][OAc] has application beyond the pretreatment of LBM as described here. Although our investigations have not included the in situ depolymerization of glucan and xylans to monomer sugars, the same process could be applied to recover monomer sugars or other materials from an IL, or for purification of ILs for other uses. Many other separations can be envisioned utilizing this solvent system or any other where the difference in interaction strengths between solvent and IL that lead to solvent displacement and a corresponding change in polarity are large enough to induce phase separation, including perhaps the concentration or separation of miscible ILs and their solutes from one another.

One open question is whether or not there are compounds that are not efficiently separated from ILs by the recycling process we have described that build up with use to levels that impact IL performance. Additional experiments are underway to characterize the IL solutes that are inefficiently removed and their impact on pretreatment efficacy during re-use of the ionic liquid for LBM pretreatment.

Conclusions

In conclusion, we have described a solvent composition with an optimum molar ratio of acetone:alcohol:IL::4-6:1:1 that does not result in the formation of gel phases during precipitation of biomass from IL solutions, but note that a 50:50 molar ratio of acetone and ethanol could be useful in other applications where gel formation from cellulose solutions in IL is a desired outcome. We have found that alcohols are more effective at reducing the IL content of precipitated LBM by washing than the acetone containing precipitation solvent, and that a combination of ethanol and water wash regimens is capable of reducing residual IL content in pre-treated corn stover to less than 0.2% (w/w). Recycling of the large volumes of wash solvent necessary to reduce IL content in precipitated biomass to low levels appears to be the most energy intensive operation in an IL pretreatment process. The recovery of a 77% of the carbohydrates present in corn stover as an easily hydrolyzed glucan-rich pretreatment product was demonstrated at the 100 gram batch scale, and two additional products were recovered from the used ionic liquid in a recycling process that resulted in impurity levels comparable to the initial IL prior to use, with the exception of water. The large number of adjustable parameters in the IL recycling process suggest that higher recycling efficiencies and yields are possible through process optimization.

EXPERIMENTAL

Chemicals. The ionic liquid (IL) 1-ethyl-3-methylimidazolium acetate, [C2mim][OAc] was purchased (Sigma-Aldrich #51053, BASF, ≥90%, Basionic™ BC01) with a typical lot specifications of >95% purity ($^1$H NMR), water content <0.3% (Karl Fischer) and used as received. Acetone was HPLC grade with specified water content ≤0.1% (Sigma-Aldrich #34850) and all other chemicals were reagent grade or better. Microcrystalline cellulose (MCC) was Avicel® PH-101 (Fluka #11365), used as received with a moisture content of 4.2 wt % measured as weight loss after drying to constant weight at 105° C.

Biomass. Corn stover (CS) was generously supplied by Drs. Bruce Dale and Venkatesh Balan at Michigan State University in knife-milled form that passed a 4 mm screen and included compositional information determined by analysis following established analytical protocols.[64] The CS contained 5.0% moisture just before use and after drying for 24 hours in a convection oven at 45° C. Complete CS compositional information is provided in Table 2. CS moisture contents were determined with an automatic moisture analyzer (Model HB 43-S, Mettler Toledo) utilizing a 10-minute 105° C. constant temperature program.

TABLE 2

Composition of corn stover and pretreated corn stover product fractions obtained from pretreatment with 1-ethyl-3-methylimidazolium acetate for 3 hours at 140° C. and subsequent recycling of the ionic liquid as described herein.

| | Percent, Extractives-Free Basis | | | | | % Ethanol | % Water | IL Content |
|---|---|---|---|---|---|---|---|---|
| | Glucan | Xylan | Arabinan | Lignin | Ash | Extractives | Extractives | % |
| Corn Stover (CS) | 33.4 | 24.8 | 3.8 | 17.2 | 3.6 | 3.3 | 7.1 | — |
| CS glucan-rich product A‡ | — | — | — | 11.3 | — | — | 18.9† | 2.7 |
| CS glucan-rich product B‡ | 45.8 | 25 | 4.8 | 9.5 | — | — | — | 0.17 |
| CS xylan-rich product† | — | — | — | 19.2 | — | — | — | 13.7 |
| CS lignin-rich product | — | — | — | 37.6 | — | — | — | — |
| CS aliphatic-rich product | 0* | 0* | 0* | — | — | — | — | — |

'—' = Not Analyzed,
* = estimated from H1 HMR
‡CS glucan-rich product B is CS glucan-rich product A after water washing
†CS xylan-rich product is the same as the CS glucan-rich product A water extractives Cellulose Dissolution and Precipitation Experiments. Two solutions of Avicel PH-101 MCC were prepared. For the first solution, used for precipitation experiments, a mixture with an overall composition of 76.9% [C2mim][OAc], 19.2% acetone, 3.7% Avicel MCC, and 0.2% moisture was obtained by mixing the MCC (4.2% moisture) with acetone, and then adding the well mixed slurry to the IL with stiffing. This mixture was stirred magnetically in a sealed 1 liter bottle placed on a hotplate/stirrer set to 35° C. for 2 weeks, resulting in a homogeneous, transparent cellulose solution. 1-2 ml of this solution was added to 13×100 mm screw-capped test tubes along with various mixtures and quantities of anhydrous acetone and ethanol, or in some cases other ketones and alcohols to give a desired overall composition, and then mixed by manually shaking. The characteristics of the precipitated cellulose or of the different solid or liquid phases present were visually inspected and noted. From these observations, a plot of precipitated cellulose characteristics as a function of ternary IL-ketone-alcohol composition was constructed and is presented in FIG. 2. The water content of these mixtures is not included in the ternary diagram, and was not measured, however atmospheric exposure was minimized to reduce moisture absorption from the ambient by the very hygroscopic IL and organic solvents.

1160 g of a second solution containing 15.5% Avicel PH-101 MCC (moisture content: 4.2%), and 84.5% [C2mim][OAc] was prepared in a stirred 1 liter glass reaction vessel with a nitrogen purge and heating mantle. The mixture of MCC and [C2mim][OAc] was heated to 80 C for 3 hours with continuous stirring, resulting in the complete dissolution of the MCC. 504.52 g of this mixture was later mixed with a mixture of 585.45 g acetone and 80.77 g methanol (to give an overall molar composition IL:Acetone:Methanol::1:4:1) to precipitate cellulose and homogenized with a laboratory rotor/stator high speed dispersion system (IKA Works, Wilmington N.C., Ultraturrax T-25, S-25-N-25G dispersion head, 17,500 rpm for 2 minutes). The thick slurry was pressure filtered over polypropylene filter cloth (#8941, Micronics) at 12 psi in a 1.5-liter reservoir pressure filter system (Model KST 142, Advantec MSF Inc.). Filtration was rapid, completing in less than 5 minutes and resulted in a powdery, compact filter cake that was easily dispersed and filtered during additional washing steps to reduce IL content. The filter cake produced following the initial precipitation operation.

Corn Stover Dissolution, Precipitation, and Washing. Corn stover (CS, 105.14 g, 5.0% moisture, 9.43 dry weight-%) was added to 959.34 g [C2mim][OAc] at 27° C. in a 1-liter glass reaction flask equipped with an electronically controlled heating mantle, thermocouple probe, continuous nitrogen purge, condenser with distillate take-off, and stiffing system with a 76 mm turbine impeller and stiffing torque monitor. Temperature of the ionic liquid slurry was ramped 140° C. and held for three hours with continuous stirring before cooling to below 60° C.

The warm, very viscous ionic liquid solution was transferred in two equal aliquots to two 1-liter glass bottles for ease of handling and mixing. To each bottle, half of a precipitation solvent solution consisting of 1 mole alcohol/mole [C2mim][OAc] plus 6 moles acetone/mole [C2mim][OAc] was added (1964 g acetone+260 g anhydrous ethanol). A high-speed rotor/stator dispersing system (IKA Works, Ultraturrax T-25, S-25-N-25G dispersion head, 17,500 rpm for 2 minutes) was used to mix the viscous IL+CS solution with the low viscosity solvent, resulting in a homogenous slurry of precipitated material. Each bottle of slurry was pressure filtered over polypropylene filter cloth (#8941, Micronics) at 12 psi in a 1.5-liter reservoir pressure filter system (Model KST 142, Advantec MSF Inc.). Filtration was rapid, completing in less than 5 minutes and resulted in a dense (21% solids), compact filter cake. Filter cakes were returned to 1-liter bottles and combined with 519.5 g of absolute ethanol (1039 g total), and dispersed and filtered as before. This ethanol wash process was repeated an additional 5 times, and the combined liquids from precipitation and ethanol wash operations combined and stored for recovery of the IL and remaining solutes.

To maximize the quantity of IL extracted from the pretreated CS solids, an additional water wash regimen was performed. To the ethanol wet pretreated CS solids from the previous operation, a total of 1039 g of water was added, the filter cakes dispersed, and the solids separated from the liquids by centrifugation (1200 RPM for 20 minutes, Beckman Coulter Avanti T-25). A total of 8 water washes were performed in this manner, with the liquids combined at the end of the operation. Centrifugation was used for solid/liquid separations for the water washes because of impractically long filtration times experienced during attempts to utilize the same filtration system used in the ethanol wash process for the water-wet material (>20 hours). The combined water washes were reduced in volume by evaporation in a convection oven at 65° C. to a solids content of 4.5%, and the IL and lignin contents determined. The water-washed slurry of pretreated CS (6.9% solids), was freeze dried (Labconco FreeZone 12) prior to analysis and saccharification experiments.

Separation and Recovery of IL and IL Solutes. The process used to recycle the IL and recover the remaining solutes from the pretreatment of corn stover generally follows the diagram in FIG. 14. The deviation in our methods from the proposed process in FIG. 14 were to accommodate the processing of a single batch at a time utilizing only common laboratory glassware and equipment and the absence of a requirement to recover the solvents used at such a small scale.

Briefly, liquid portions collected from the CS precipitation and ethanol washing steps were combined and distilled at atmospheric pressure under nitrogen to remove acetone, and most of the alcohol (Distillation Column A in FIG. 14). The remaining liquid was extracted with 4 aliquots of 400 mL of dry acetone (Extraction Solvent A in FIG. 14) to remove oleophillic substances and some of the IL from the remaining liquid. This first extractant was transferred to a 2-liter separatory funnel and 100 ml water added to cause a second, lower phase to form containing nearly all of the IL dissolved in the acetone extractant. The upper layer, containing acetone and non-polar substances was reduced in volume by distillation, and then dried in a vacuum oven to give a brown, greasy semi-solid containing approximately 2% of the original CS dry weight, the Aliphatic-Rich Product in FIG. 14.

A second extraction of the remaining ionic liquid from Distillation Column A in FIG. 14 was performed with 5 aliquots of 400 mL of a mixture of acetone+4% anhydrous 2-propanol, leaving a viscous black liquid. The first (acetone) and second (acetone+2-propanol) extracts were combined and reduced in volume by distillation, and then dried at 115° C. in a vacuum oven for 12 hours to yield 89% of the original IL mass. The extracted viscous black liquid was rinsed out of the separatory funnels with a minimum of 2-propanol (approximately 20 ml) and centrifuged to separate precipitated solids. These solid were washed with 3×20 ml of additional 2-propanol and set aside. The 2-propanol wash liquids were combined, concentrated at 40° C. under vacuum and additional material precipitated by the addition of a few mL of 2-propanol. This precipitate was washed 3 times with a minimum of 2-propanol, and again concentrated under vacuum. The process of precipitation, centrifugation, and washing was repeated a total of 4 times, at diminishing volumes and yielding decreasing amounts of solid precipitate. The precipitated solids were combined and dried under vacuum at 40° C. to yield a brown powder with approximately 4% of the original CS dry weight, indicated as the Lignin-Rich Product in FIG. 14.

Composition of Pretreated Corn Stover. CS structural carbohydrate content after IL pretreatment, including cellulose, xylan, arabinan, and galactan, were determined after a two-step acid hydrolysis performed according to established analytical procedures.[64] Carbohydrates were analyzed by HPAEC (Dionex ICS-3000) equipped with an electrochemical detector and a 4×250 mm CarboPac PA20 analytical column (Dionex).[65] Elution was initiated with 97.2% (v/v) water and 2.8% (v/v) 1 M NaOH for first 15 min, with 20 µL injection volume. Elute concentration was then switched to 55.0% (v/v) water and 45.0% (v/v) 1 M NaOH for next 20 min and returned to 97.2% (v/v) water and 2.8% (v/v) 1M NaOH for the last 10 min to equilibrate the column. The flow rate was 0.5 mL/min.

The lignin content of pretreated CS and the lignin-rich IL extract was determined with a modified acetyl bromide method.[66] Biomass powder (5 mg) was treated with 25% (w/w) acetyl bromide in glacial acetic acid (0.2 mL). The tubes were sealed and incubated at 50° C. for 2 h at 1050 rpm on a thermomixer (SI-1200, Scientific Industries, Inc.). After digestion, the solutions were diluted with three volumes of acetic acid, and 0.1 mL was transferred to 15 mL centrifuge tubes with addition of another 0.5 mL acetic acid. The solutions were mixed well, and then 0.3 M sodium hydroxide (0.3 mL) and 0.5 M hydroxylamine hydrochloride (0.1 mL) were added. The final volume was increased to 2 mL by addition of acetic acid and UV spectra of solutions were measured against a blank prepared using the same method. Lignin content was determined by absorbance at 280 nm utilizing an extinction coefficient of 17.747 L g$^{-1}$ cm$^{-1}$.[67]

Enzymatic Hydrolysis. Enzymatic hydrolysis of freeze-dried pretreated biomass was carried out at 50° C. and 150 rpm in a reciprocating shaker. For pretreated CS, a glucan loading of 30 g/L deionized water was used for saccharification (6.57% CS solids). A total batch volume of 30 mL was used with a cellulase (Novozymes, NS50013, 70 FPU/g) concentration of 50 mg protein/g glucan and β-glucosidase (Novozymes, NS50010, 250 egu/g) concentration of 5 mg protein/g glucan. The reaction was monitored by withdrawing 100 µL samples at specific time intervals, followed by centrifugation at 10,000 g for 5 minutes and measuring reducing sugar content by DNS assay using D-glucose as a standard.[68] All assays were performed in duplicate.

Measurement of IL Content. [C2mim] [OAc] content in enzyme hydrolyzed CS was quantified by HPLC/MS (ref) (model 1100 LC/MSD Quad SL, Agilent Technologies Inc.) using a Zorbax Eclipse Plus C8 reverse phase column (150× 4.6 mm, 3.5 µm particle size; Agilent Technologies Inc.). The elution was performed via isocratic elution of a mobile phase consisting of 20 mM ammonium acetate and 0.2% formic acid in an acetonitrile/water solution (20:80 v/v %). All solvents were HPLC grade purity (Honeywell Burdick & Jackson). The flow-rate and temperature were maintained at 0.5 ml/min and 35° C., respectively. The [C2mim] cation was detected using pneumatically assisted electrospray in positive scan and SIM mode with a dwell time of 600 msec. The mass spectrometer parameters were: 4 kV capillary voltage, 10 L/min drying gas flow-rate, 20 psi nebulizer pressure, and 300° C. drying gas temperature.

NMR Spectroscopy. $^1$H NMR spectra was acquired on a Bruker Advance 600 MHz spectrometer equipped with a TCI Cryoprobe. Samples were prepared by adding 13% w/w DMSO-d6 to approximately 1 ml of as-received and recycled [C2mim] [OAc] in 5 mm sample tubes and mixed thoroughly. A 45 minute spectra consisting of 256 scans of 4096 points was collected with a relaxation delay of 10 seconds at 33° C. DMSO at $\delta_H$ 2.49 ppm was used as an internal standard.

REFERENCES

1. R. D. Perlack, L. L. Wright, A. F. Turhollow, R. L. Graham, B. J. Stokes, D. C. Erbach, Biomass as Feedstock for A Bioenergy and Bioproducts Industry: The Technical Feasibility of a Billion-Ton Annual Supply, United States Department of Energy and United States Department of Agriculture Report #ADA436753, April 2005. Available at http://handle.dtic.mil/100.2/ADA436753
2. M. Parikka, Global biomass fuel resources, *Biomass Bioenergy* (2004) 27 613-620
3. J. Fargione, J. Hill, D. Tilman, S. Polasky, P. Hawthorne, Land Clearing and the Biofuel Carbon Debt *Science* (2008) 319 1235-1238
4. M. M. Wright, R. C. Brown, Comparative economics of biorefineries based on the biochemical and thermochemical platforms, *Biofuels, Bioprod. Biorefin.* (2007) 1 49-56
5. B. Yang, C. E. Wyman, Pretreatment: the key to unlocking low-cost cellulosic ethanol, *Biofuels, Bioprod. Biorefin.* (2007) 2 26-40
6. A. T. W. M. Hendriks, G. Zeeman, Pretreatments to enhance the digestibility of lignocellulosic biomass *Bioresour. Technol.* (2009) 100 10-18
7. N. Mosier, C. Wyman, B. Dale, R. Elander, Y. Y. Lee, M. Holtzapple, M. Ladisch, Features of promising technologies for pretreatment of lignocellulosic biomass *Bioresour. Technol.* (2005) 96 673-686
8. R. T. Elander, B. E. Dale, M. Holtzapple, M. R. Ladisch, Y. Y. Lee, C. Mitchinson, J. N. Saddler, C. E. Wyman, Summary of findings from the Biomass Refining Consortium for Applied Fundamentals and Innovation (CAFI): corn stover pretreatment *Cellulose* (2009) 16 649-659
9. L. C. Sousa, S. P S. Chundawat, V. Balan, B. E. Dale, 'Cradle-to-grave' assessment of existing lignocellulose pretreatment technologies *Curr. Opin. Biotechnol.* (2009) 20 339-347
10. Y. Zheng, Z. Pan, R. Zhang, Overview of biomass pretreatment for cellulosic ethanol production *Int. J. Agric. & Biol. Eng.* (2009) 2 No. 3 51-68
11. O. A. El Seoud, A. Koschella, L. C. Fidale, S. Dorn, T. Heinze, Applications of Ionic Liquids in Carbohydrate Chemistry: A Window of Opportunities *Biomacromolecules* (2007) 8 No. 9 2629-2647
12. S. S. Y. Tan, D. R. MacFarlane, Ionic Liquids in Biomass Processing *Top. Curr. Chem.* (2009) 290 311-339
13. M. E. Zakrzewska, E. Bogel-Łukasik, R. Bogel-Łukasik, Solubility of Carbohydrates in Ionic Liquids *Energy Fuels* (2010) 24 737-745
14. D. A. Fort, R. C. Remsing, R. P. Swatloski, P. Moyna, G. Moyna, R. D. Rogers, Can ionic liquids dissolve wood? Processing and analysis of lignocellulosic materials with 1-n-butyl-3-methylimidazolium chloride *Green Chem.* (2007) 9 63-69
15. H. Zhao, C. L. Jones, G. A. Baker, S. Xia, O. Olubajo, V. N. Person, Regenerating cellulose from ionic liquids for an accelerated enzymatic hydrolysis *J. Biotechnol.* (2009) 139 47-54
16. C. Li, B. Knierim, C. Manisseri, R. Arora, H. V. Scheller, M. Auer, K. P. Vogel, B. A. Simmons, S. Singh Comparison of dilute acid and ionic liquid pretreatment of switchgrass: Biomass recalcitrance, delignification, and enzymatic saccharification *Bioresour. Technol.* (2010) 101 4900-4906
17. I. P. Samayam, C. A. Schall, Saccharification of ionic liquid pretreated biomass with commercial enzyme mixtures *Bioresour. Technol.* (2010) 101 3561-3566
18. N. Sun, M. Rahman, Y. Qin, M. L. Maxim, H. Rodríguez, R. D. Rogers, Complete dissolution and partial delignification of wood in the ionic liquid 1-ethyl-3-methylimidazolium acetate *Green Chem.* (2009) 11 646-655
19. S. Dorn, F. Wendler, F. Meister, T. Heinze, Interactions of Ionic Liquids with Polysaccharides-7: Thermal Stability of Cellulose in Ionic Liquids and N-Methylmorpholine-N-Oxide *Macromol. Mater. Eng.* (2008) 293 907-913
20. F. Hermanutz, F. Gahr, E. Uerdingen, F. Meister, B. Kosan, New Developments in Dissolving and Processing of Cellulose in Ionic Liquids *Macromol. Symp.* (2008) 262 23-27
21. I. Kilpeläinen, H. Xie, A. King, M. Granstrom, S. Heikkinen, D. S. Argyropoulos, Dissolution of Wood in Ionic Liquids *J. Agric. Food Chem.* (2007) δ 9142-9148
22. B. Li, J. Asikkala, I. Filpponen, D. S. Argyropoulos, Factors Affecting Wood Dissolution and Regeneration of Ionic Liquids *Ind. Eng. Chem. Res.* (2010) 49 2477-2484
23. M. Zavrel, D. Bross, M. Funke, J. Büchs, A. C. Spiess, High-throughput screening for ionic liquids dissolving (ligno-)cellulose *Bioresour. Technol.* (2009) 100 2580-2587
24. Q. Li, Y.-C. He, M. Xian, G. Jun, X. Xu, J.-M. Yang, L.-Z. Li, Improving enzymatic hydrolysis of wheat straw using ionic liquid 1-ethyl-3-methyl imidazolium diethyl phosphate pretreatment *Bioresour. Technol.* (2009) 100 3570-3575
25. D. M. Phillips, L. F. Drummy, D. G. Conrady, D. M. Fox, R. R. Naik, M. O, Stone, P. C. Trulove, H. C. De Long, R. A. Mantz, Dissolution and Regeneration of *Bombyx mori* Silk Fibroin Using Ionic Liquids *J. Am. Chem. Soc.* (2004) 126 14350-14351
26. H. Garcia, R. Ferreira, M. Petkovic, J. L. Ferguson, M. C. Leitão, H. Q. N. Gunaratne, K. R. Seddon, L. P. N. Rebelo, C. S Pereira, Dissolution of cork biopolymers in biocompatible ionic liquids *Green Chem.* (2010) 12 367-369
27. Y. Wu, T. Sasaki, S. Irie, K. Sakurai, A novel biomass-ionic liquid platform for the utilization of native chitin *Polymer* (2008) 49 2321-2327
28. H. Xie, S. L1, S. Zhang, Ionic liquids as novel solvents for the dissolution and blending of wool keratin fibers *Green Chem.* (2005) 7 606-608
29. N. Kamiya, Y. Matsushita, M. Hanaki, K. Nakashima, M. Narita, M. Goto, H. Takahashi, Enzymatic in situ saccharification of cellulose in aqueous-ionic liquid media *Biotechnol. Lett.* (2008) 30 1037-1040
30. C. Li, Q. Wang, Z. K. Zhao, Acid in ionic liquid: An efficient system for hydrolysis of lignocellulose *Green Chem.* (2008) 10 177-182
31. Y. Zhang, J. Y. G. Chan, Sustainable chemistry: imidazolium salts in biomass conversion and $CO_2$ fixation *Energy Environ. Sci.* (2010) 3 408-417
32. H. Zhao, J. E. Holladay, H. Brown, Z. C. Zhang, Metal Chlorides in Ionic Liquid Solvents Convert Sugars to 5-Hydroxymethylfurfural *Science* (2007) 316 1597-1600
33. M. Mazza, D.-A. Catana, C. Vaca-Garcia, C. Cecutti, Influence of water on the dissolution of cellulose in selected ionic liquids *Cellulose* (2009) 16 207-215
34. H. G. Joglekar, I. Rahman, B. D. Kulkarni, The Path Ahead for Ionic Liquids *Chem. Eng. Technol.* (2007) 30 No. 7 819-828
35. K. E. Gutowski, G. A. Broker, H. D. Willauer, J. G. Huddleston, R. P. Swatloski, J. D. Holbrey, R. D. Rogers, Controlling the Aqueous Miscibility of Ionic Liquids: Aqueous Biphasic Systems of Water-Miscible Ionic Liquids and Water-Structuring Salts for Recycle, Metathesis, and Separations *J. Am. Chem. Soc.* (2003) 125 6632-6633
36. S. Li, C. He, H. Liu, K. Li, F. Liu, Ionic liquid-based aqueous two-phase system, a sample pretreatment procedure prior to high-performance liquid chromatography of opium alkaloids *J. Chromatogr. B* (2005) 826 58-62

37. T. C. Brennan, S. Datta, H. W. Blanch, B. A. Simmons, B. M. Holmes, Recovery of Sugars from Ionic Liquid Biomass Liquor by Solvent Extraction *Bioenerg. Res.* (2010) 3 123-133

38. 42. X. Honglu, S. Tiejun, Wood liquefaction by ionic liquids *Holzforschung* (2006) 60 509-512

39. B. Li, I. Filpponen, D. S. Argyropoulos, Acidolysis of Wood in Ionic Liquids *Ind. Eng. Chem. Res.* (2010) 49 3126-3136

40. H. Rodríguez, M. Francisco, M. Rahman, N. Sun, R. D. Rogers, Biphasic liquid mixtures of ionic liquids and polyethylene glycols *Phys. Chem. Chem. Phys.* (2009) 11 10916-10922

41. H. Rodríguez, R. D. Rogers, Liquid mixtures of ionic liquids and polymers as solvent systems *Fluid Phase Equilibr.* (2010) DOI 10.1016/j.fluid.2009.12.036

42. T.-A. D. Nguyen, K.-R. Kim, S. J. Han, H. Y. Cho, J. W. Kim, S. M Park, J. C. Park, S. J. Sim, Pretreatment of rice straw with ammonia and ionic liquid for lignocellulose conversion to fermentable sugars *Bioresour. Technol.* (2010) 7432-7438

43. O. Aaltonen, O. Jauhiainen, The preparation of lignocellulosic aerogels from ionic liquid solutions *Carbohydr. Polym.* (2009) 75 125-129

44. J. Kadokawa, M. Murakami, Y. Kaneko, A facile preparation of gel materials from a solution of cellulose in ionic liquid *Carbohydr. Res.* (2008) 343 769-772

45. A. Pinkert, K. N. Marsh, S. Pang, M. P. Staiger, Ionic Liquids and Their Interaction with Cellulose *Chem. Rev.* (2009) 109 6712-6728

46. C. D. Tran, S. H. De Paoli Lacerda, D. Oliveira, Absorption of Water by Room-Temperature Ionic Liquids Effect of Anions on Concentration and State of Water *Appl. Spectrosc.* (2003) 57 No. 2 152-157

47. J. Vitz, T. Erdmenger, C. Haensch, U.S. Schubert, Extended dissolution studies of cellulose in imidazolium based ionic liquids *Green Chem.* (2009) 11 417-424

48. N. P. Novoselov, E. S. Sashina, O. G. Kuz'mina, S. V. Troshenkova, Ionic Liquids and Their Use for the Dissolution of Natural Polymers *Russ. J. Gen. Chem.* (2007) 77 No. 8 1395-1405

49. N. P. Novoselov, E. S. Sashina, V. E. Petrenko, M. Zaborsky, Study of Dissolution of Cellulose in Ionic Liquids by Computer Modeling *Fibre Chem.* (2007) 39 No. 2 153-158

50. S. V. Troshenkova, E. S. Sashina, N. P. Novoselov, K.-F. Arndt, S. Jankowsky, Structure of Ionic Liquids on the Basis of Imidazole and Their Mixtures with Water *Russ. J. Gen. Chem.* (2010) 80 No. 1 106-111

51. V. K. Verma, T. Banerjee, Ionic liquids as entrainers for water+ethanol, water+2-propanol, and water+THF systems: A quantum chemical approach *J. Chem. Thermodyn.* (2010) 42 909-919

52. L. Zhang, J. Han, D. Deng, J. Ji, Selection of ionic liquids as entrainers for separation of water and 2-propanol *Fluid Phase Equilib.* (2007) 255 179-185

53. F. Montañés, A. Olano, E. Ibaez, T. Formari, Modeling Solubilities of Sugars in Alcohols Based on Original Experimental Data *AIChE J.* (2007) 53 No. 9 2411-2418

54. J. M. B. Fernandes Diniz, M. H. Gil, J. A. A. M. Castro, Hornification—its origin and interpretation in wood pulps *Wood Sci. Technol.* (2004) 37 489-494

55. M. A. Hubbe, R. A. Venditti, 0. J. Rojas, What Happens to Cellulosic Fibers During Papermaking and Recycling? A Review. *Bioresources* (2007) 2 No. 4, 739-788

56. T. Köhnke, K. Lund, H. Brelid, G. Westman, Kraft pulp hornification: A closer look at the preventive effect gained by glucuronoxylan adsorption *Carbohydr. Polym.* (2010) 81 226-233

57. M. Deng, Q. Zhou, A. Du, J. van Kasteren, Y. Wang, Preparation of nanoporous cellulose foams from cellulose-ionic liquid solutions *Mater. Lett.* (2009) 63 1851-1854

58. C. S. R. Freire, P. C. R. Pinto, A. S. Santiago, A. J. D. Silvestre, D. V. Evtuguin, C. P. Neto, Comparative study of lipophilic extractives of hardwoods and corresponding ECF bleached kraft pulps *Bioresources* (2006) 1 No. 1, 3-17

59. J. Yan, Z. Hu, Y. Pu, E. C. Brummer, A. J. Ragauskas, Chemical compositions of four switchgrass populations *Biomass Bioenergy* (2010) 34 48-53

60. K. Thammasouk, D. Tandjo, M. H. Penner, Influence of Extractives on the Analysis of Herbaceous Biomass *J. Agric. Food Chem.* (1997) 45 437-443

61. A. K. Burrell, R. E. Del Sesto, S, N. Baker, T. M. McCleskey, G. A. Baker, The large scale synthesis of pure imidazolium and pyrrolidinium ionic liquids *Green Chem.* (2007) 9 449-454

62. B. Clare, A. Sirwardana, D. R. MacFarlane, Synthesis, Purification and Characterization of Ionic Liquids *Top. Curr. Chem.* (2009) 290 1-40

63. S. F. Chen, R. A. Mowery, R. S. Sevcik, C. J. Scarlata, C. K. Chambliss, Compositional Analysis of Water-Soluble Materials in Switchgrass *J. Agric. Food Chem.* (2010) DOI:10.1021/jf9033877

64. A. Sluiter, B. Hames, R. Ruiz, C. Scarlata, J. Sluiter, D. Templeton (2004) Determination of Structural Carbohydrates and Lignin in Biomass. LAP-002, NREL Laboratory Standard Analytical Procedures, National Renewably Energy Laboratory, Golden Colo. http://www.nrel.gov/biomass/analytical_procedures.html 65. J. Øbro, J. Harholt, H. V. Scheller, C. Orfila, Rhamnogalacturonan I in *Solanum tuberosum* tubers contains complex arabinogalactan structures *Phytochemistry* (2004) 65 1429-1438

66. K. K. Pandey, A. J. Pitman, Examination of the Lignin Content in a Softwood and a Hardwood Decayed by a Brown-Rot Fungus with the Acetyl Bromide Method and Fourier Transform Infrared Spectroscopy *J. Polym. Sci., Part A: Polym. Chem.* (2004) 42 2340-2346

67. R. S. Fukushima, R. D. Hatfield, Comparison of the Acetyl Bromide Spectrophotometric Method with Other Analytical Lignin Methods for Determining Lignin Concentration in Forage Samples *J. Agric. Food Chem.* (2004) 52 3713-3720

68. G. L. Miller, Use of dinitrosalicylic acid reagent for determination of reducing sugar *Anal. Chem.* (1959) 31 426-428

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A composition comprising (a) a first liquid phase comprising a water-miscible ionic liquid (IL), a ketone, and a biomass, lignin, cellulose, or lignocellulosic biomass (LBM); and (b) a solid or second liquid phase comprising an alcohol; wherein the composition has a molar ratio X:Y:Z:: ketone: the alcohol: the IL, wherein the molar ratio X:Y:Z is defined by the area labeled "Porous Solid+Liquid" in FIG. 3.

2. The composition of claim 1, wherein the IL is 1-alkyl-3-alkylimidazolium alkanate, 1-alkyl-3-alkylimidazolium alkylsulfate, 1-alkyl-3-alkylimidazolium methylsulfonate, 1-alkyl-3-alkylimidazolium hydrogensulfate, 1-alkyl-3-alkylimidazolium thiocyanate, and 1-alkyl-3-alkylimidazolium halide, wherein "alkyl" is an alkyl group comprising from 1 to 10 carbon atoms, and "alkanate" is an alkanate comprising from 1 to 10 carbon atoms.

3. The composition of claim 1, wherein the IL is 1-ethyl-3-methylimidazolium acetate (EMIN Acetate), 1-ethyl-3-methylimidazolium chloride (EMIN Cl), 1-ethyl-3-methylimidazolium hydrogensulfate (EMIM HOSO3), 1-ethyl-3-methylimidazolium methylsulfate (EMIM MeOSO3), 1-ethyl-3-methylimidazolium ethylsulfate (EMIM EtOSO3), 1-ethyl-3-methylimidazolium methanesulfonate (EMIM MeSO3), 1-ethyl-3-methylimidazolium tetrachloroaluminate (EMIM AlCl4), 1-ethyl-3-methylimidazolium thiocyanate (EMIM SCN), 1-butyl-3-methylimidazolium acetate (BMIM Acetate), 1-butyl-3-methylimidazolium chloride (BMIM Cl), 1-butyl-3-methylimidazolium hydrogensulfate (BMIM HOSO3), 1-butyl-3-methylimidazolium methanesulfonate (BMIM MeSO3), 1-butyl-3-methylimidazolium methylsulfate (BMIM MeOSO3), 1-butyl-3-methylimidazolium tetrachloroaluminate (BMIM AlCl4), 1-butyl-3-methylimidazolium thiocyanate (BMIM SCN), 1-ethyl-2,3-dimethylimidazolium ethylsulfate (EDIM EtOSO3), Tris(2-hydroxyethyl)methylammonium methylsulfate (MTEOA MeOSO3), 1-methylimidazolium chloride (MIM Cl), 1-methylimidazolium hydrogensulfate (MIM HOSO3), 1,2,4-trimethylpyrazolium methylsulfate, tributylmethylammonium methylsulfate, choline acetate, or choline salicylate.

4. The composition of claim 1, wherein the ketone is acetone, dimethyl ketone, methyl-ethyl ketone, diethyl ketone, or a mixture thereof.

5. The composition of claim 4, wherein the ketone is acetone.

6. The composition of claim 1, wherein the alcohol is methanol, ethanol, propanol, butanol, or a mixture thereof.

7. The composition of claim 6, wherein the alcohol is ethanol.

8. The composition of claim 1, wherein the molar ratio X:Y:Z is about $X>3$, $0.8<Y<1.2$, and $Z=1$.

9. The composition of claim 8, wherein the molar ratio X:Y:Z is about $3.3 \leq X \leq 8$, $Y \approx 1$, and $Z=1$.

10. The composition of claim 9, wherein the molar ratio X:Y:Z is about $4 \leq X \leq 6$, $Y=1$, and $Z=1$.

\* \* \* \* \*